United States Patent
Padia

(10) Patent No.: US 11,634,415 B2
(45) Date of Patent: Apr. 25, 2023

(54) DERIVATIVES OF SUBSTITUTED MORPHOLINES AND USES THEREOF

(71) Applicant: Supernus Pharmaceuticals, Inc., Rockville, MD (US)

(72) Inventor: Janak Khimchand Padia, Germantown, MD (US)

(73) Assignee: Supernus Pharmaceuticals, Inc., Rockville, MD (US)

( * ) Notice: Subject to any disclaimer, the term of this patent is extended or adjusted under 35 U.S.C. 154(b) by 0 days.

(21) Appl. No.: 17/824,644

(22) Filed: May 25, 2022

(65) Prior Publication Data

US 2022/0298150 A1    Sep. 22, 2022

Related U.S. Application Data

(63) Continuation of application No. 17/698,592, filed on Mar. 18, 2022.

(60) Provisional application No. 63/162,671, filed on Mar. 18, 2021.

(51) Int. Cl.
  *C07D 413/12* (2006.01)
  *C07D 265/30* (2006.01)
  *C07D 413/14* (2006.01)

(52) U.S. Cl.
  CPC ......... *C07D 413/12* (2013.01); *C07D 265/30* (2013.01); *C07D 413/14* (2013.01)

(58) Field of Classification Search
  CPC .......................... C07D 413/12; C07D 265/30
  See application file for complete search history.

(56) References Cited

U.S. PATENT DOCUMENTS

2009/0325956 A1    12/2009    Taniguchi et al.

FOREIGN PATENT DOCUMENTS

| EP | 2 558 437 A2 | 2/2013 | | |
| GB | 1243991 A | * | 8/1971 | ........... C07D 211/22 |
| GB | 1 260 886 A | | 1/1972 | |
| WO | WO-9822110 A1 | * | 5/1998 | ........... C07D 211/74 |

OTHER PUBLICATIONS

Boot et al., "Discovery and structure-activity relationships of novel selective norepinephrine and dual serotonin/norepinephrine reuptake inhibitors," Bioorganic & Medicinal Chemistry Letters, Feb. 1, 2005, 15(3):699-703.

Brenner et al., "Asymmetric Synthesis of (+)-(S,S)-Reboxetine via a New (S)-2-(Hydroxymethyl)morpholine Preparation," Organic Letters, Jan. 25, 2005, 7(5):937-939.

International Search Report and Written Opinion dated Sep. 22, 2022 in PCT/US2022/020976.

Letavic et al., "2-Aryloxymethylmorpholine histamine H"3 antagonists," Bioorganic & Medicinal Chemistry Letters, Nov. 1, 2008, 18(21):5796-5799.

Fish et al., "Design and synthesis of morpholine derivatives. SAR for dual serotonin & nonadrenaline reuptake inhibition," Bioorganic & Medicinal Chemistry Letters, 2008, 18:2562-2566.

Fish et al., "Enantioselective synthesis of (R)- and (S)-N-Boc-morpholine-2-carboxylic acids by enzyme-catalyzed kinetic resolution: application to the synthesis of reboxetine analogs," Tetrahedron Letters, Jan. 28, 2009, 50(4):389-391.

Invitation to Pay Additional Fees and Partial International Search Report dated Jun. 27, 2022 in PCT PCT/US2022/020976.

Jobson et al., "Stereoselective synthesis of (2S,3R)- and (2R,3S)-iodoreboxetine; potential SPECT imaging agents for the nonadrenaline transporter," Organic & Biomolecular Chemistry, 2008, 6(13):2369-2376.

Melloni et al., "Potential antidepressant agents. Alpha-Aryloxybenzyl derivatives of ethanolamine and morpholine," Eur. J. Med. Chem.—Chim. Ther., 1984, 19(3):235-242.

Metro et al., "Syntheses of (S,S)-Reboxetine via a Catalytic Stereospecific Rearrangement of Beta-Amino Alcohols," The Journal of Organic Chemistry, Dec. 20, 2007, 73(2):707-710.

Yu et al., "Metabolism and in vitro drug-drug interaction assessment of viloxazine," Xenobiotica, Jun. 10, 2020, 50(11):1285-1300.

* cited by examiner

*Primary Examiner* — Samira J Jean-Louis

(74) *Attorney, Agent, or Firm* — Foley & Lardner LLP

(57) ABSTRACT

A compound of Formula I includes a stereoisomer thereof and/or a salt thereof; wherein $R^1$ is a substituted alkane group, a heterocylic group, or a pyridine group; X is hydrogen, a halogen, an amino acid residue, a substituted amino acid residue, an alkyl group, or an ester. Such compounds may be used in pharmaceutical compositions and for the treatment of central nervous system (CNS) disorders:

(I)

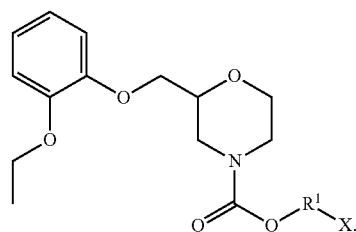

29 Claims, No Drawings

DERIVATIVES OF SUBSTITUTED MORPHOLINES AND USES THEREOF

CROSS-REFERENCE TO RELATED APPLICATIONS

This application is a Continuation of U.S. application Ser. No. 17/698,592, filed Mar. 18, 2022, claims priority to U.S. Provisional Application No. 63/162,671, filed Mar. 18, 2021, the entire contents of which are incorporated herein.

FIELD

The present technology generally relates to derivatives of substituted morpholines and their uses in pharmaceutical compositions and for the treatment of central nervous system (CNS) disorders.

BACKGROUND (R,S)-2-[(2-ethoxyphenoxy)methyl]morpholine:

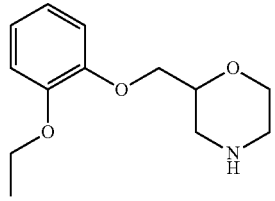 [SMILES: CCOc1ccccc1OCC1CNCCO1]

is a bicyclic morpholine derivative, assigned CAS No. 46817-91-8 (CAS No. 35604-67-2 for the HCl salt). It is characterized by the formula $C_{13}H_{19}NO_3$, with a molecular mass of 237.295 g/mol.

2-((2-ethoxyphenoxy)methyl)morpholine is known to have several desirable pharmacologic uses, including treatment of depression, nocturnal enuresis, narcolepsy, sleep disorders, and alcoholism, among others. 2-((2-ethoxyphenoxy)methyl)morpholine was previously marketed in several European countries for the treatment of major depressive disorder (MDD). 2-((2-ethoxyphenoxy)methyl)morpholine is an inhibitor of the reuptake of norepinephrine ("NRI"), but may also enhance the release of serotonin from neuronal stores.

However, treatment with 2-((2-ethoxyphenoxy)methyl)morpholine has been associated with numerous side effects including nausea, vomiting, loss of appetite, increased erythrocyte sedimentation, EKG and EEG anomalies, epigastric pain, diarrhea, constipation, vertigo, orthostatic hypotension, edema of the lower extremities, dysarthria, tremor, psychomotor agitation, mental confusion, inappropriate secretion of antidiuretic hormone, increased transaminases, and seizure.

In order to minimize the side effects associated with 2-((2-ethoxyphenoxy)methyl)morpholine, chemists have synthesized derivatives and analogs that retain the pharmacologic properties of 2-((2-ethoxyphenoxy)methyl)morpholine. Derivatives of substituted morpholines have been previously disclosed in the art, for example in UK Patent 1 243 391 and UK Patent 1 260 886. In a different approach, the present inventors synthesize novel derivatives of substituted morpholines. Prodrugs are a class of derivatives that in many instances have little or no pharmacological activity, which are converted in vivo to therapeutically active compounds. In some instances, the prodrug itself may possess biological activity. Prodrug activation may occur by enzymatic or non-enzymatic cleavage of the temporary bond between the carrier and the drug molecule, or a sequential or simultaneous combination of both.

The newly synthesized derivatives of substituted morpholines, with the derivatization of the amine group of the morpholine in the structure of 2-((2-ethoxyphenoxy)methyl) morpholine produce chemically stable compounds to serve as novel compounds. These derivatives of 2-((2-ethoxyphenoxy)methyl)morpholine can be used in pharmaceutical compositions and for the treatment of central nervous system (CNS) disorders.

SUMMARY

In one aspect, derivatives of substituted morpholines are provided, including a compound of Formula I, a stereoisomer thereof, or a salt thereof:

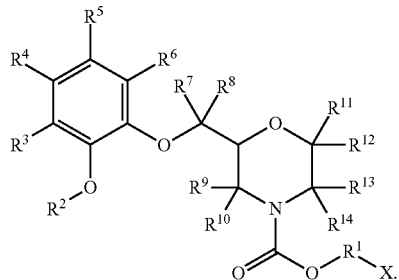

In Formula I, $R^1$ may be alkyl, heterocylyl, or a pyridyl, $R^2$ may be alkyl, aryl, heteroaryl, or heterocyclyl, $R^3$-$R^{14}$ may be each independently H, F, Cl, Br, I, CN, $NO_2$, alkyl, aryl, heteroaryl, or heterocyclyl; and X may be H, F, Cl, Br, I, an amino acid residue, a substituted amino acid residue, alkyl, ester.

In some embodiments, the present technology relates to derivatives of substituted morpholines according to the compound of Formula II, stereoisomer thereof, and/or a salt thereof:

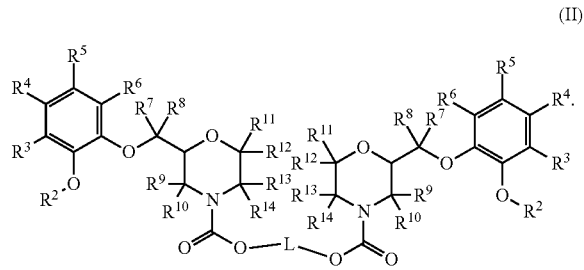

In Formula II, L may be alkyl, a substituted pyridinecarboxylic acid, or a substituted azanediyl acetate; $R^2$ may be alkyl, aryl, heteroaryl, or heterocyclyl; and $R^3$-$R^{14}$ may be each independently H, F, Cl, Br, I, CN, $NO_2$, alkyl, aryl, heteroaryl, or heterocyclyl.

In some embodiments, the present technology relates to derivatives of substituted morpholines according to the compound of Formula III, a stereoisomer thereof, and/or a salt thereof:

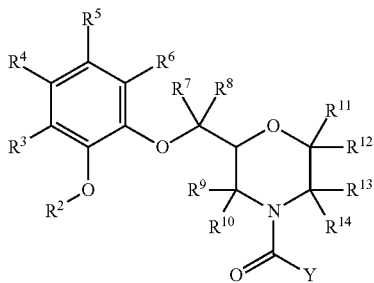

(III)

In Formula III, Y may be F, Cl, Br, I, an amino acid residue, a substituted amino acid residue, alkyl, or ester; $R^2$ may be alkyl, aryl, heteroaryl, or heterocyclyl; and $R^3$-$R^{14}$ may be each independently H, F, Cl, Br, I, CN, $NO_2$, alkyl, aryl, heteroaryl, or heterocyclyl.

In some embodiments, derivatives of substituted morpholines are provided according to Formula IV, a stereoisomer thereof, and/or a salt thereof:

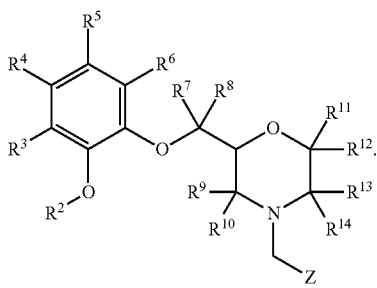

(IV)

In Formula IV, Z may be H, F, Cl, Br, I, an amino acid residue, a substituted amino acid residue, or a nitrogen-containing group; $R^2$ may be alkyl, aryl, heteroaryl, or heterocyclyl; and $R^3$-$R^{14}$ may be each independently H, F, Cl, Br, I, CN, $NO_2$, alkyl, aryl, heteroaryl, or heterocyclyl.

In any of the above embodiments, $R^2$ may be $CH_2CH_3$. In any of the above embodiments, $R^3$-$R^{14}$ may each be H.

In some aspects, a composition is provided that includes derivatives of substituted morpholines of Formula I, II, III, or IV, their stereoisomers and/or salts thereof and at least one pharmaceutically acceptable excipient or carrier.

In some aspects, treatment of a central nervous system ("CNS") disorder is provided, the treatment including administering to a subject in need thereof a pharmaceutical composition that includes a derivative of substituted morpholines, including of a compound of Formula I, II, III, or IV.

In some aspects, a method is provided for making a derivative of substituted morpholines, including of a compound of Formula I, II, III, or IV, their stereoisomers and/or salts thereof comprising contacting 2-((2-ethoxyphenoxy)methyl)morpholine or a salt thereof, Intermediate 1, Intermediate 2, or Intermediate 3 with a reactive compound suitable for forming the compound of Formula I, II, III, or IV.

DETAILED DESCRIPTION

Definitions. The following terms are used throughout as defined below.

As used herein, the term "viloxazine" or 2-((2-ethoxyphenoxy)methyl)morpholine means (R,S)-2-[(2-ethoxyphenoxy)methyl]morpholine] includes a pharmaceutically acceptable salt or ester thereof, including either a single (−) enantiomer or a single (+) enantiomer, or in the form of a racemic mixture or a non-racemic mixture of enantiomers with varying amounts of (−) and (+) enantiomers.

As used herein and in the appended claims, singular articles such as "a" and "an" and "the" and similar referents in the context of describing the elements (especially in the context of the following claims) are to be construed to cover both the singular and the plural, unless otherwise indicated herein or clearly contradicted by context. Recitation of ranges of values herein merely intended to serve as shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

Generally, reference to a certain element such as hydrogen or H is meant to include all isotopes of that element. For example, if an R group is defined to include hydrogen or H, it also includes deuterium and tritium. Compounds comprising radioisotopes such as tritium, $C^{14}$, $P^{32}$, and $S^{35}$ are thus within the scope of the present technology. Procedures for inserting such labels into the compounds of the present technology will be readily apparent to those skilled in the art based on the disclosure herein.

In general, "substituted" refers to an organic group as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group is substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls; alkoxy, alkenoxy, aryloxy, aralkyloxy, heterocyclyl, heterocyclylalkyl, heterocyclyloxy, and heterocyclylalkoxy groups; carbonyls (oxo); carboxylates; esters; urethanes; oximes; hydroxylamines; alkoxyamines; aralkoxyamines; thiols; sulfides; sulfoxides; sulfones; sulfonyls; pentafluorosulfanyl (i.e., $SF_5$), sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like.

The term "carboxylate" as used herein refers to the conjugate base a carboxylic acid with the chemical formula —COO.

The term "ester" as used herein refers to —COOR²— and —C(O)O-G groups. R² is a substituted or unsubstituted alkyl, cycloalkyl, alkenyl, alkynyl, aryl, aralkyl, heterocyclylalkyl or heterocyclyl group as defined herein. G is a carboxylate protecting group. Carboxylate protecting groups are well known to one of ordinary skill in the art. An extensive list of protecting groups for the carboxylate group functionality may be found in Protective Groups in Organic Synthesis, Greene, T. W.; Wuts, P. G. M., John Wiley & Sons, New York, N.Y., (3rd Edition, 1999) which can be added or removed using the procedures set forth therein and which is hereby incorporated by reference in its entirety and for any and all purposes as if fully set forth herein.

The term "amide" (or "amido") includes C- and N-amide groups, i.e., C(O)NR³R⁴, and —NRC(O)—R groups, respectively. R³ and R⁴ are independently hydrogen, or a substituted or unsubstituted alkyl, alkenyl, alkynyl, cycloalkyl, aryl, aralkyl, heterocyclylalkyl or heterocyclyl group as defined herein. Amido groups therefore include but are not limited to carbamoyl groups (—C(O)NH₂) and formamide groups (NHC(O)H). In some embodiments, the amide is —NRC(O)—(C₁₋₅ alkyl) and the group is termed "carbonylamino," and in others the amide is —NHC(O)-alkyl and the group is termed "alkanoylamino."

The term "amine" (or "amino") as used herein refers to —NR⁵R⁶ groups, wherein R⁵ and R⁶ are independently hydrogen, or a substituted or unsubstituted alkyl, alkenyl, alkynyl, cycloalkyl, aryl, aralkyl, heterocyclylalkyl or heterocyclyl group as defined herein. In some embodiments, the amine is alkylamino, dialkylamino, arylamino, or alkylarylamino. In other embodiments, the amine is NH₂, methylamino, dimethylamino, ethylamino, diethylamino, propylamino, isopropylamino, phenylamino, or benzylamino.

The term "halogen" or "halo" as used herein refers to bromine (Br), chlorine (Cl), fluorine (F), or iodine (I). In some embodiments, the halogen is chlorine (Cl).

The term "polypeptide" or "peptide" as used herein refers to two or more amino acids linked by a peptide (i.e., amide) bond between the carboxyl terminus of one amino acid and the amino terminus of another. The term "peptide" may be combined with a prefix indicating the number of amino acids in the peptide, e.g., a "pentapeptide" is a peptide of five amino acids.

The term "amino acid" is recognized in the art and generally refers to a natural or unnatural alpha or beta amino acid. The term "amino acid" includes, but is not limited to, anyone of the twenty-one standard L-amino acids commonly found in naturally occurring peptides.

The term "amino acid residue with hydrophobic side chain" as used herein refers to the following amino acids: alanine (Ala), valine (Val), isoleucine (Ile), Leucine (Leu), methionine (Met), phenylalanine (Phe), tyrosine (Tyr), tryptophan (Trp). In some embodiment, the amino acid residue with hydrophobic side chain is valine (Val). In other embodiment, the amino acid residue with hydrophobic side chain is phenylalanine (Phe).

The term "acetyl" as used herein refers to a methyl group bonded to a carbonyl group (CH₃CO—).

The term "pyridine" group as used herein refers to a group with the heterocyclic organic compound with the chemical formula C₅H₅N.

The term "pyridinecarboxylic acid" as used herein refers to compound having a pyridine ring and a carboxyl group.

The term "azanediyl" as used herein refers to a functional group having the formula —NH; the group is bonded to the rest of the compound by two single bonds.

Pharmaceutically acceptable salts of compounds described herein are within the scope of the present technology and include acid or base addition salts which retain the desired pharmacological activity and is not biologically undesirable (e.g., the salt is not unduly toxic, allergenic, or irritating, and is bioavailable). When the compound of the present technology has a basic group, such as, for example, an amino group, pharmaceutically acceptable salts can be formed with inorganic acids (such as hydrochloric acid, hydroboric acid, nitric acid, sulfuric acid, and phosphoric acid), organic acids (e.g., alginate, formic acid, acetic acid, benzoic acid, gluconic acid, fumaric acid, oxalic acid, tartaric acid, lactic acid, maleic acid, citric acid, succinic acid, malic acid, methanesulfonic acid, benzenesulfonic acid, naphthalene sulfonic acid, and p-toluenesulfonic acid) or acidic amino acids (such as aspartic acid and glutamic acid). When the compound of the present technology has an acidic group, such as for example, a carboxylic acid group, it can form salts with metals, such as alkali and earth alkali metals (e.g., Na⁺, Li⁺, K⁺, Ca²⁺, Mg²⁺, or Zn²⁺), ammonia or organic amines (e.g., dicyclohexylamine, trimethylamine, triethylamine, pyridine, picoline, ethanolamine, diethanolamine, or triethanolamine) or basic amino acids (e.g. arginine, lysine, or ornithine). Such salts can be prepared in situ during isolation and purification of the compounds or by separately reacting the purified compound in its free base or free acid form with a suitable acid or base, respectively, and isolating the salt thus formed.

Stereoisomers of compounds (also known as optical isomers) include all chiral, diastereomeric, and racemic forms of a structure, unless the specific stereochemistry is expressly indicated. Thus, compounds used in the present technology include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these stereoisomers are all within the scope of the present technology.

The term "pharmaceutically acceptable excipient" refers to those substances that are well accepted by the industry and regulatory agencies such as those listed in monographs published in compendia such as USP-NF, Food Chemicals Codex, Code of Federal Regulations (CFR), FDA Inactive Ingredients Guide and in 21 CFR parts 182 and 184 that lists substances that are generally regarded as safe (GRAS) food ingredients.

In one aspect, a compound represented by Formula I is provided, or a stereoisomer thereof or a pharmaceutically acceptable salt thereof:

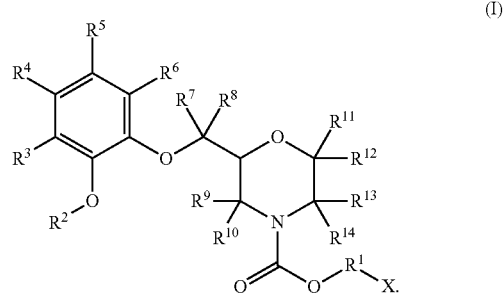

(I)

In the compound of Formula I, R¹ may be alkyl, heterocylyl, or a pyridyl; R² may be alkyl, aryl, heteroaryl, or heterocyclyl; $R^3$-$R^{14}$ may be each independently H, F, Cl, Br, I, CN, $NO_2$, alkyl, aryl, heteroaryl, or heterocyclyl; and X may be H, halogen, an amino acid residue, a substituted amino acid residue, alkyl, ester. In some preferred embodiments, $R^2$ is ethyl. In any of the above embodiments, $R^1$ may be $CH_2$, $CH_2CH_2$, $CH_2CH_2CH_2$, $CH_2CH_2CH_2CH_2$, $(CH_3)_2C$, $(CH_3)_2CHCH_2$, or $(CH_3)_3CCH_2$. In any of the above embodiments, X may be an amino acid residue. In such embodiments, the amino acid residue may further include a hydrophobic side chain. In any of the above embodiments, the amino acid residue may be valine or phenylalanine. In any of the above embodiments, each of $R^3$-$R^{14}$ may be independently H, F, Cl, Br, I, or alkyl. In some such embodiments, each of $R^3$-$R^{14}$ may be independently H or $C_1$-$C_6$ alkyl. In some embodiments, $R^3$-$R^{14}$ are all H. In any of the above embodiments, $R^1$ may be $CH_2CH_2$ or $CH_2CH_2CH_2CH_2$. In various embodiments above, $R_1$ may be $CH_2$ or $C_2H_5$, and/or X may be an ester. In various embodiments above, $R^1$ may be a pyridyl group and X may be F, Cl, Br, or I.

In various embodiments, the compound represented by Formula I is one or more of the following compounds, with the understanding that where chiral centers are present each representation includes any R, S, or racemic structures as well:

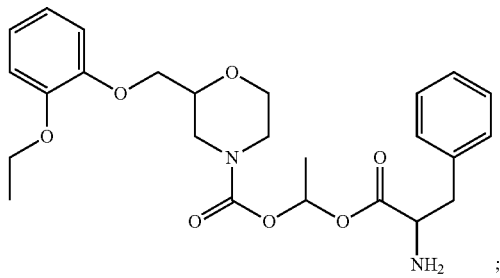

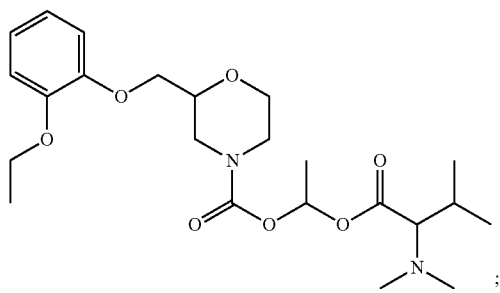

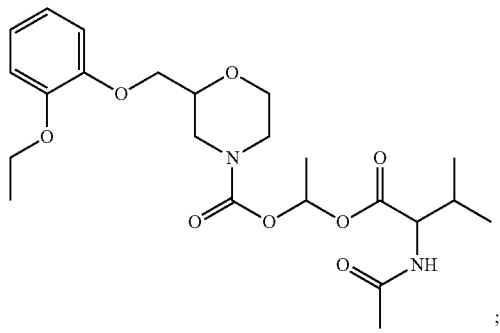

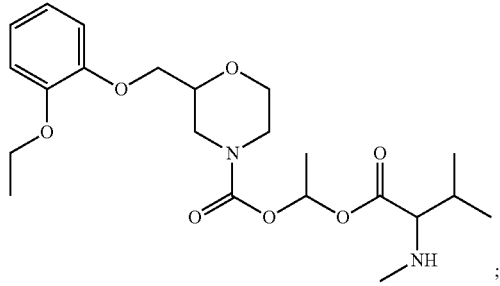

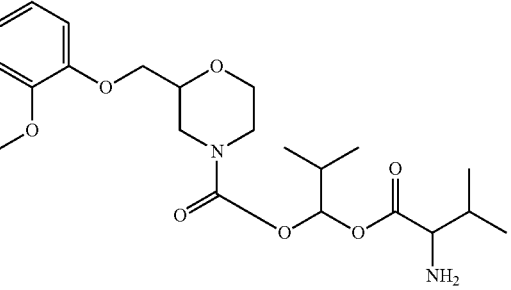

-continued

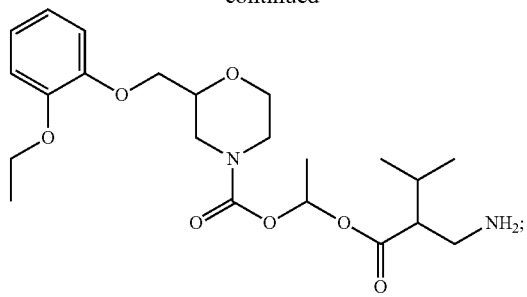

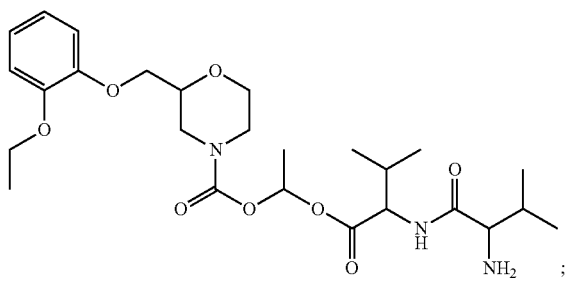

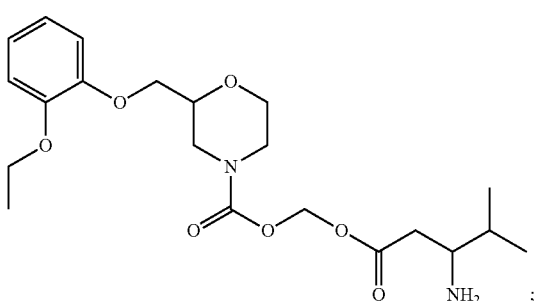

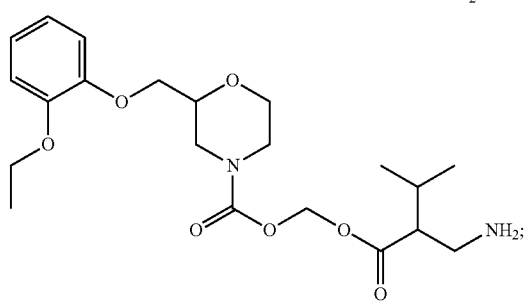

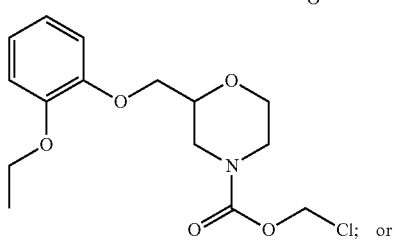

Cl; or

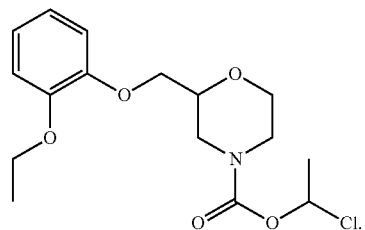

Cl.

In some embodiments, the compound represented by Formula I is:

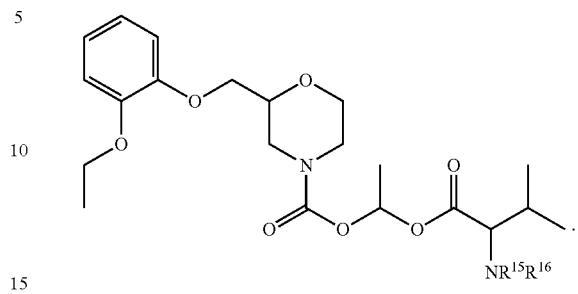

In the above formula, $R^{15}$ may be H, alkyl, or —C(O)OR$^{17}$; $R^{16}$ may be H, alkyl, or —C(O)OR$^{17}$; and $R^{17}$ may be H or alkyl. In some embodiments, $R^{15}$ may be alkyl and $R^{16}$ may be H or alkyl. In such embodiments, $R^{15}$ may be methyl and $R^{16}$ may be H or methyl. In some embodiments, $R^{15}$ and $R^{16}$ are methyl. In some embodiments, $R^{15}$ is —C(O)OR$^{17}$, $R^{16}$ is H, and $R^{17}$ is methyl.

In another aspect, a compound represented by Formula II is provided, or a stereoisomer thereof, and/or a salt thereof:

(II)

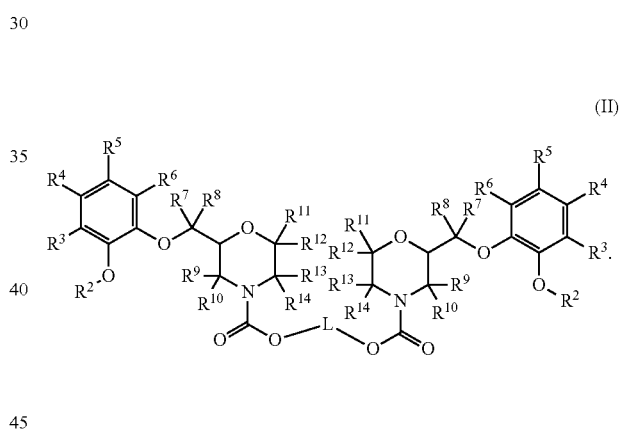

In Formula II, L is alkyl, a substituted pyridinecarboxylic acid, or a substituted azanediyl acetate; $R^2$ is alkyl, aryl, heteroaryl, or heterocyclyl; and $R^3$-$R^{14}$ are each independently H, F, Cl, Br, I, CN, NO$_2$, alkyl, aryl, heteroaryl, or heterocyclyl. In some embodiments, $R^2$ is ethyl.

In some embodiments, the compound represented by Formula II is:

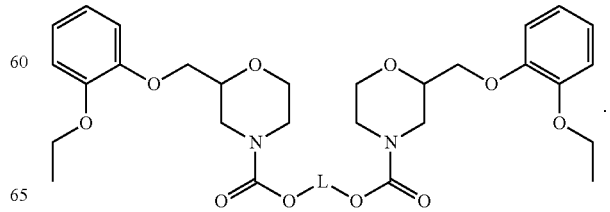

In various embodiments, the compound of Formula II is one or more of the following:

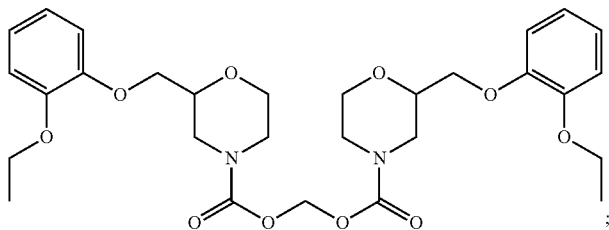

(SP-21)

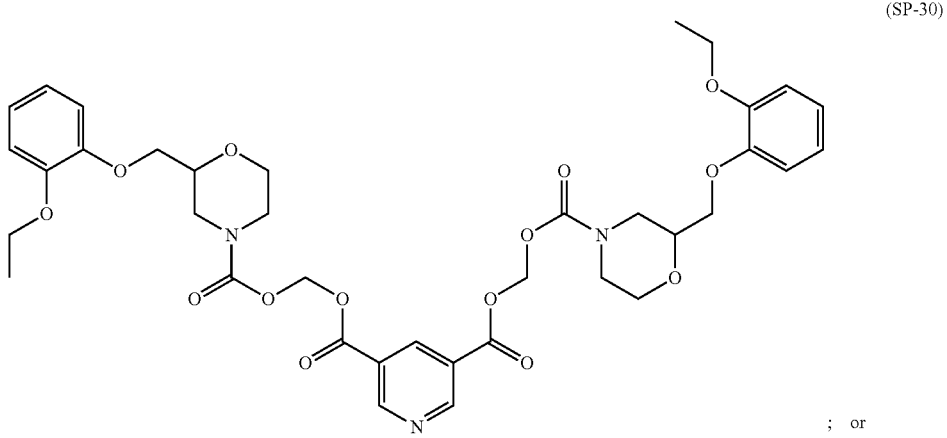

(SP-30)

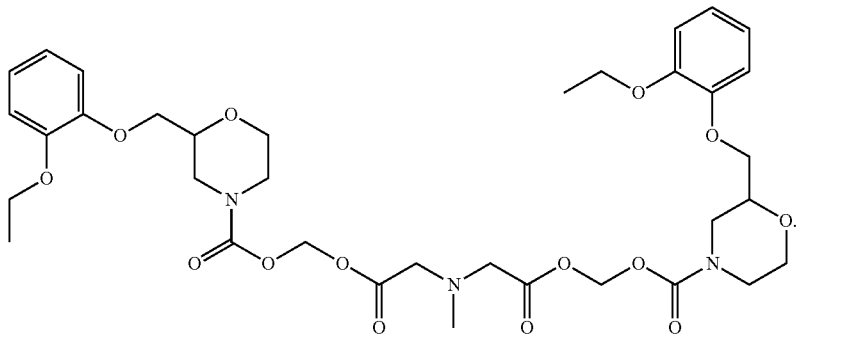

(SP-31)

In another aspect, a compound represented by Formula III is provided, or a stereoisomer thereof, and/or a salt thereof:

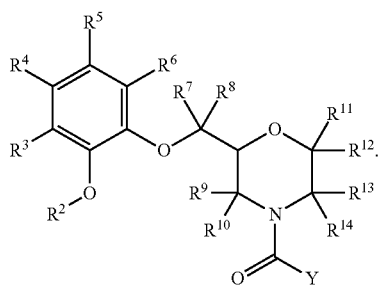

(III)

In Formula III, Y may be F, Cl, Br, I, an amino acid residue, a substituted amino acid residue, alkyl, or ester; $R^2$ may be alkyl, aryl, heteroaryl, or heterocyclyl; and $R^3$-$R^{14}$ may be each independently H, F, Cl, Br, I, CN, $NO_2$, alkyl, aryl, heteroaryl, or heterocyclyl. In some embodiments, $R^2$ is ethyl.

In some embodiments, the compound represented by Formula III is:

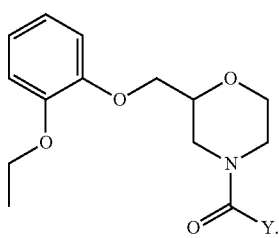

In some embodiments, the compound represented by Formula III is:

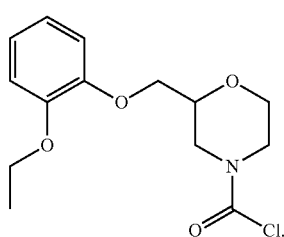

(Intermediate 1)

In another aspect, a compound represented by Formula IV is provided, or a stereoisomer thereof, and/or a salt thereof:

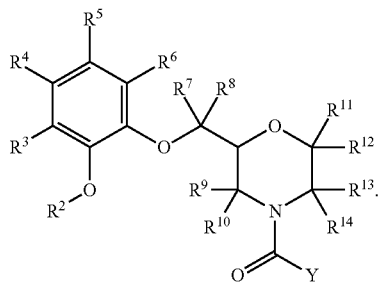

(III)

In Formula III, Z may be H, F, Cl, Br, I, an amino acid residue, a substituted amino acid residue, or a nitrogen-containing group; $R^2$ may be alkyl, aryl, heteroaryl, or heterocyclyl; and $R^3$-$R^{14}$ may be each independently H, F, Cl, Br, I, CN, $NO_2$, alkyl, aryl, heteroaryl, or heterocyclyl. In some embodiments, $R^2$ is ethyl.

In some embodiments, the compound represented by Formula IV is:

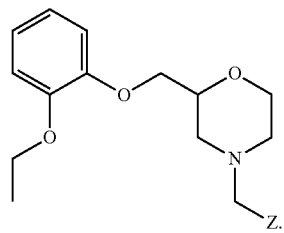

(SP-18)

In some embodiments, the compound represented by Formula IV is:

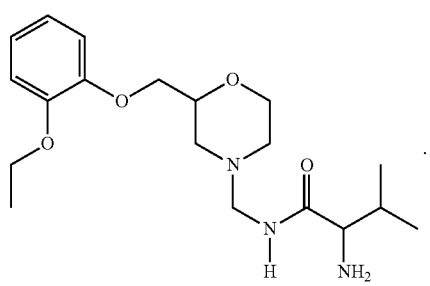

In some embodiments, a composition includes a derivative of substituted morpholines of Formula I, II, III, or IV, stereoisomers thereof, and/or salts thereof, and at least one pharmaceutically acceptable excipient or carrier.

In some embodiments, a pharmaceutical composition includes comprising a a derivative of substituted morpholines of Formula I, II, III, or IV, stereoisomers thereof, and/or salts thereof with a pharmaceutically acceptable carrier or excipient. The pharmaceutical formulation may be in an appropriate dosage form. Illustrative dosage forms include, but are not limited to, injections, oral forms, suppositories, caches, pouches, transdermal, and the like.

In another aspect, treatment of a CNS disorder is provided by administering a composition including a derivative of substituted morpholines of Formulae I, II, III, or IV, or salts thereof as described herein to a subject in need thereof.

In another aspect, a method is provided for administering to a subject a composition including a compound of Formula I, II, III, or IV or salts thereof. In one aspect, the subject is a mammal. In further embodiments, the mammalian subject is a human. In particular embodiments, the mammalian subject is an adult human or a human child.

In some embodiments, the methods described herein include administering the derivative of substituted morpholines of Formula I, II, III, or IV, stereoisomers thereof, and/or salts thereof along with at least one additional pharmaceutical agent. In some embodiments, the at least one additional pharmaceutical agent is another agent for a CNS disorder. In further embodiments, the at least one additional pharmaceutical agent is 2-((2-ethoxyphenoxy)methyl)morpholine or a salt thereof.

In one embodiment, the derivative of substituted morpholines may be prepared from 2-((2-ethoxyphenoxy)methyl)morpholine or a salt thereof.

In one embodiment, the derivative of substituted morpholines may be prepared by reacting 2-((2-ethoxyphenoxy)methyl)morpholine or a salt thereof with sodium bicarbonate to form the intermediate 1 having the following structure:

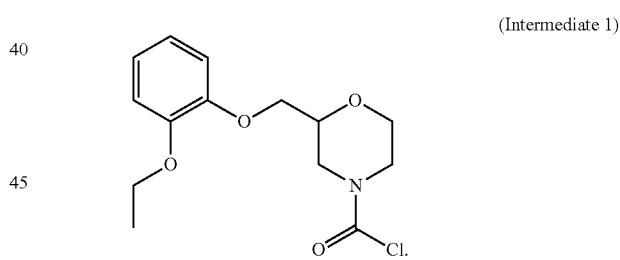

(Intermediate 1)

In one embodiment, the derivative of substituted morpholines may be prepared by reacting 2-((2-ethoxyphenoxy)methyl)morpholine or a salt thereof with 1-chloromethyl chloroformate forming the Intermediate 2 having the following structure:

(Intermediate 2)

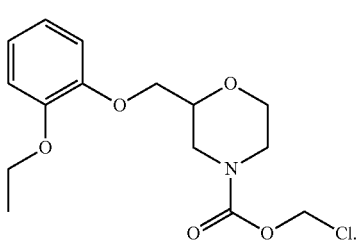

In one embodiment, the derivative of substituted morpholines can be prepared by reacting 2-((2-ethoxyphenoxy)methyl)morpholine or a salt thereof with 1-chloroethyl chloroformate forming the Intermediate 3 having the following structure:

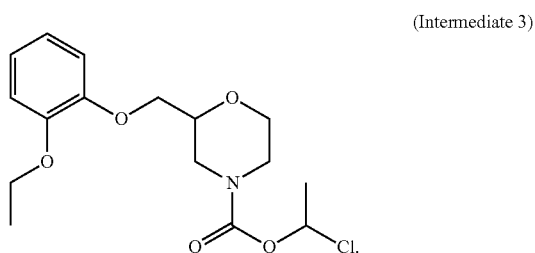 [SMILES: CCOc1ccccc1OCC1CN(C(=O)OC(C)Cl)CCO1]

(Intermediate 3)

In one embodiment, the derivatives of substituted morpholines of Formula I, II, III, or IV are prepared by reacting 2-((2-ethoxyphenoxy)methyl)morpholine or a salt thereof with the Intermediate 1, Intermediate 2, or Intermediate 3.

In another embodiment, a method of making the derivatives of substituted morpholines of Formula I, II, III, or IV are provided.

The derivatives of substituted morpholines may be analyzed by liquid chromatography-mass spectrometry (LCMS) and nuclear magnetic resonance (NMR) spectroscopy.

The present invention, thus generally described, will be understood more readily by reference to the following examples, which are provided by way of illustration and are not intended to be limiting of the present invention.

EXAMPLES

Procedures for making the Intermediates. It is understood that while in some structures, chiral centers are indicated in either an R or S configuration, the other configuration is also disclosed herein.

Intermediate 1: Synthesis of 2-((2-ethoxyphenoxy)methyl)morpholine-4-carbonyl chloride.

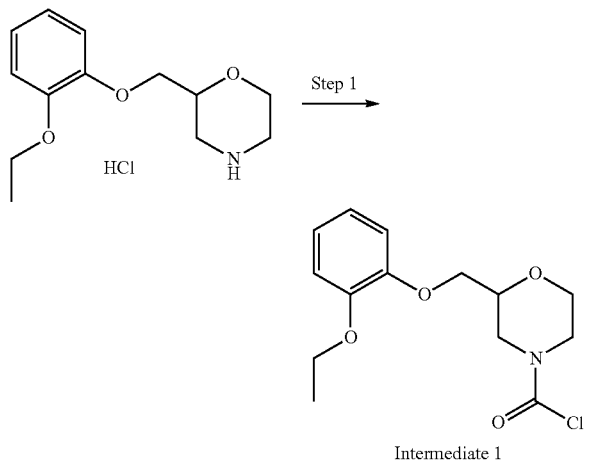

A solution of 2-((2-ethoxyphenoxy)methyl)-morpholine hydrochloride (500 mg, 1.83 mmol) in dichloromethane (50 ml) was added dropwise to a slurry of sodium bicarbonate (460 mg, 5.48 mmol). The reaction mixture was stirred for 30 minutes. A solution of triphosgene (358 mg, 1.21 mmol) in dichloromethane (25 ml) was added at 10-15° C. over 15 minutes. The reaction mixture was stirred at room temperature for 3 hours. The reaction mass was filtered to remove sodium chloride and the filtrate is concentrated under vacuum to give 438 mg of ethyl methyl carbamoyl chloride as a light yellow oil (yield: 80%).

$^1$H NMR (CDCl$_3$, 400 MHz): δ ppm 6.88-6.91 (m, 4H), 4.39-4.47 (br t, 1H), 3.96-4.25 (m, 6H), 3.83-3.87 (br t, 1H), 3.61-3.71 (br t, 1H), 3.03-3.38 (m, 2H), 1.44 (t, 3H).

Intermediate 2: chloromethyl 2-((2-ethoxyphenoxy)methyl)morpholine-4-carboxylate.

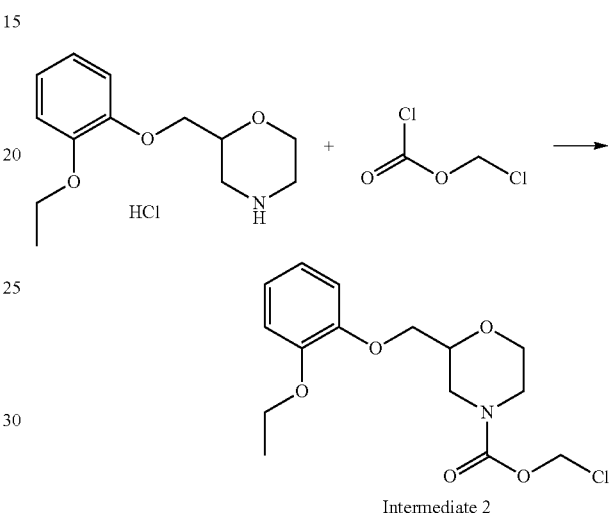

Intermediate 2

To a stirred ice cold mixture of 2-((2-ethoxyphenoxy)methyl)morpholine hydrochloride (1.3 gm, 4.52 mmol), trimethylamine (1.01 gm, 9.95 mmol) dichloromethane was added dropwise 1-chloromethyl chloroformate. The reaction mixture was stirred at 10-15° C., allowed to attain room temperature and stirred for 5 hours. The precipitated solids were filtered and the filtrate was concentrated. The crude product was purified by column chromatography (hexane: EtOAc 7:3) to afford 1.2 gm (80%) of white solid.

$^1$H NMR (CDCl$_3$, 400 MHz): δ ppm 1.46 (t, 3H), 1.59 (s, 4H), 3.05 (d, 2H), 3.63 (d, 1H), 3.92-4.02 (m, 2H), 4.04-4.15 (m, 4H), 4.23 (br. s., 1H), 5.76-5.86 (m, 2H), 6.84-7.00 (m, 4H).

Intermediate 3: 1-chloroethyl 2-((2-ethoxyphenoxy)methyl)morpholine-4-carboxylate.

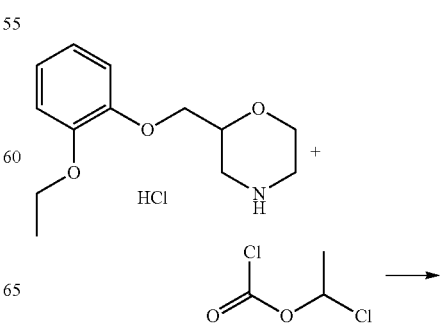

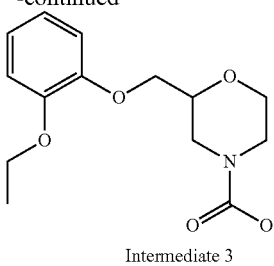

Intermediate 3

To a stirred ice cold mixture of 2-((2-ethoxyphenoxy)-methyl)morpholine hydrochloride (2 gm, 6.96 mmol), trimethylamine (1.01 g, 9.95 mmol) dichloromethane was added dropwise 1-chloroethyl chloroformate (1.19 g, 83.5 mmol). The reaction mixture was stirred at 10-15° C. and allowed to attain room temperature and stirred for 5 h. Precipitated solids were filtered and the filtrate was concentrated. The crude product was purified by column chromatography (hexane:EtOAc 7:3) to afford 1.42 gm (59.3%) of white solid.

$^1$H NMR (400 MHz, CDCl$_3$): δ ppm 1.39-1.51 (m, 3H), 1.83 (d, 3H), 2.92-3.12 (m, 2H), 3.54-3.72 (m, 1H), 3.85 (br. s., 1H), 3.89-4.13 (m, 7H), 4.20 (d, 1H), 6.61 (m, 1H), 6.84-7.01 (m, 4H).

Procedures for Synthesizing the Compounds of Formula I, II, III or IV:

SP-16: ((D-valyl)oxy)methyl 2-((2-ethoxyphenoxy)methyl)morpholine-4 carboxylate.

Step 1.

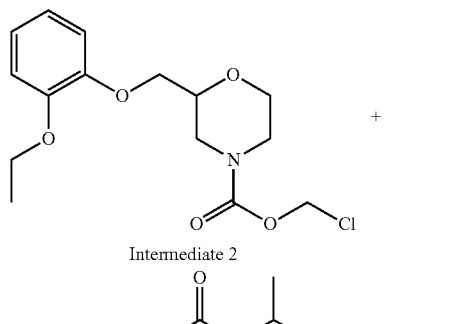

Intermediate 2

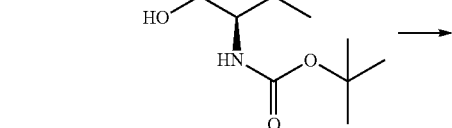

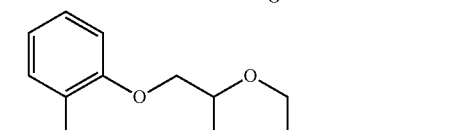

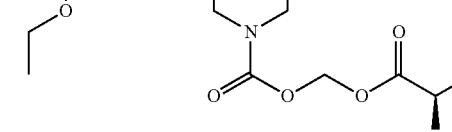

SP-16A

A reaction mixture of N-Boc-D-Valine (175 mg, 0.80 mmol), cesium carbonate (130 mg, 0.4 mmol), in methanol (3.3 ml) was stirred at room temperature for 3 hours, then methanol evaporated, residue reconstituted with DMF (1 ml). To the reaction mixture was added chloromethyl 2-((2-ethoxyphenoxy)methyl)morpholine-4-carboxylate (Intermediate 2) (177 mg, 0.52 mmol). The resulting mixture was stirred at 80° C. for 20 hours. DMF was evaporated under vacuum, residue dissolved in chloroform and purified by column chromatography (hexane:EtOAc 1:1) to afford 112 mg (39.4%) of semi-solid oil.

Step 2:

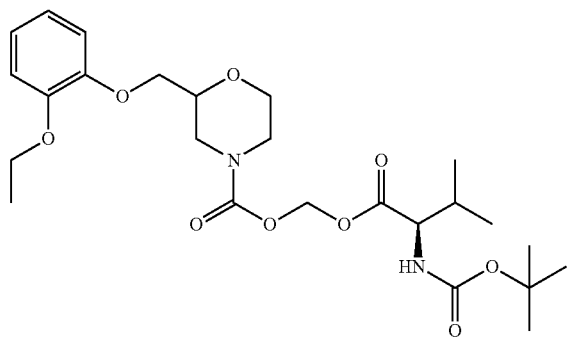

SP-16A

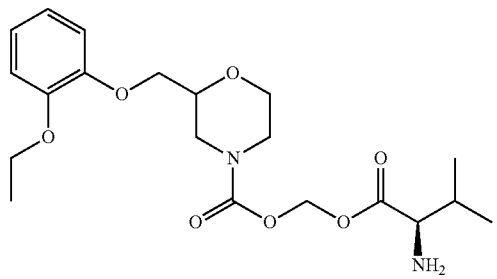

SP-16

A solution of SP-16A (65 mg, 0.12 mmol) and 2M HCl in dioxane stirred at room temperature overnight. Solvent was evaporated and dried under vacuum to obtain 50 mg (95.6%) of pure desired product (SP-16) as a brown semisolid. LCMS: Purity: 96.27% by ELS detector. MS: M+H=411.14. $^1$H NMR (CDCl$_3$, 400 MHz): δ ppm 1.12 (t, 6H), 1.44 (t, 3H), 2.46 (br. s, 1H), 2.90-3.10 (m, 2H), 3.52-3.66 (m, 1H), 3.85-420 (m, 10H), 5.83 (br. s, 1H), 5.95 (d, 1H), 6.85-6.96 (m, 4H), 8.24 (br. s, 2H).

SP-17: 1-((L-valyl)oxy)ethyl 2-((2-ethoxyphenoxy)methyl)morpholine-4 carboxylate.

Step 1.

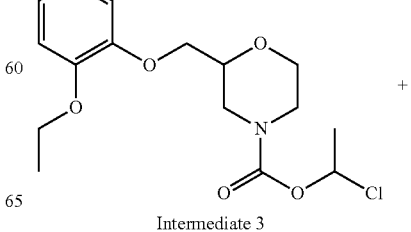

Intermediate 3

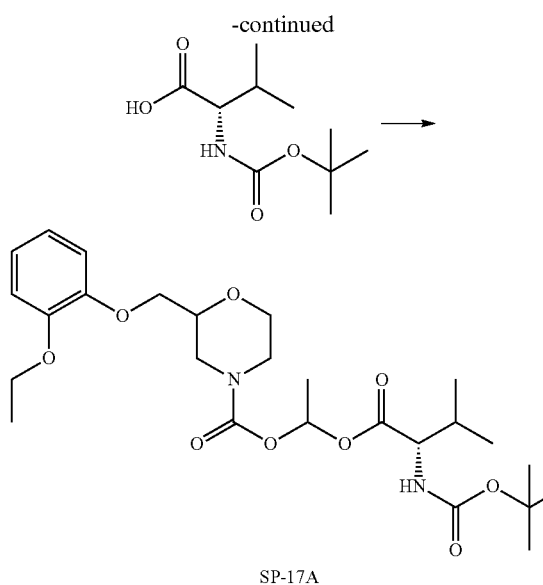

SP-17A

A reaction mixture of N-Boc-L-Valine (175 mg, 0.80 mmol), cesium carbonate (130 mg, 0.4 mmol), in methanol (3.3 ml) was stirred at room temperature for 3 hours, then methanol evaporated, residue reconstituted with DMF (1 ml). To the reaction mixture was added chloromethyl 2 1-chloroethyl 2-((2-ethoxyphenoxy)methyl)morpholine-4-carboxylate (Intermediate 3) (184 mg, 0.52 mmol). The resulting mixture was stirred at 80° C. for 20 hours. DMF was evaporated under vacuum, residue dissolved in chloroform and purified by column chromatography (hexane: EtOAc 8:2) to obtain 141 mg (48.3%) of semisolid oil.

Step 2:

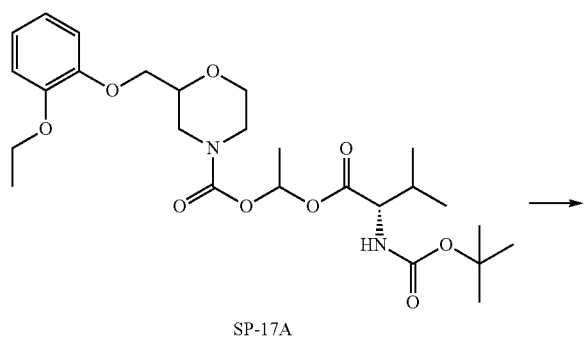

SP-17A

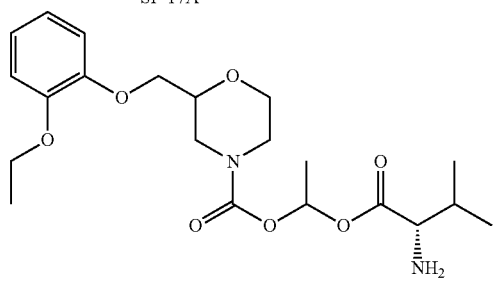

SP-17

A solution of SP-17A (65 mg, 0.11 mmol) and 2M HCl in dioxane stirred at room temperature overnight. The solvent was then evaporated and the product dried under vacuum to obtain 51 mg (92.4%) of pure desired product (SP-17) as a brown solid. LCMS: Purity: 100% by ELS detector. MS: M+H=425.17. ¹H NMR (CDCl₃, 400 MHz): δ ppm 1.12 (t, 6H), 1.44 (t, 3H), 2.46 (br. s., 1H), 2.90-3.10 (m, 2H), 3.52-3.66 (m, 1H), 3.85-420 (m, 10H), 5.83 (br. s., 1H), 5.95 (d, 1H), 6.85-6.96 (m, 4H), 8.24 (br. s, 2H).

SP-18: (2R)-2-amino-N-((2-((2-ethoxyphenoxy)methyl)morpholino)methyl)-3-methylbutanamide bis hydrochloride salt.

Step 1:

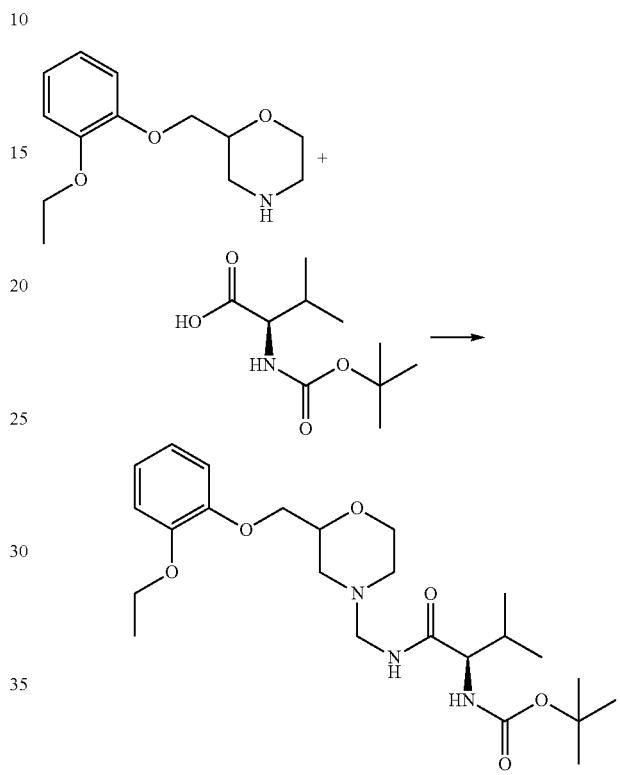

SP-18A

To a solution of 2-((2-ethoxyphenoxy)methyl)-morpholine hydrochloride (108 mg, 0.4 mmol) and polyformaldehyde (50 mg) in THF (2 ml) was added a slurry of sodium bicarbonate (92 mg, 1.1 mmol). The reaction mixture was stirred for 48 hours minutes. The reaction mass was filtered and the filtrate was concentrated under vacuum. The residue was dissolved in chloroform and purified by column chromatography (hexane: EtOAc 8:1) to obtain 80 mg (43%) of semi-solid oil.

Step 2:

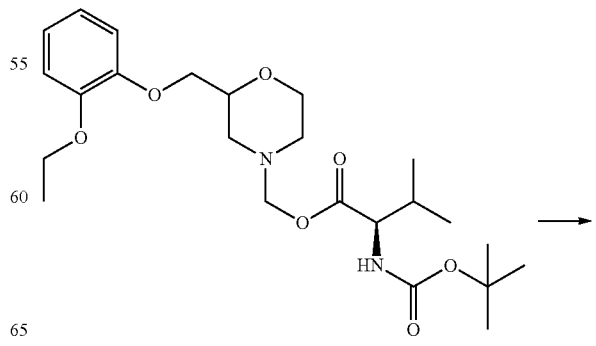

SP-18A

-continued

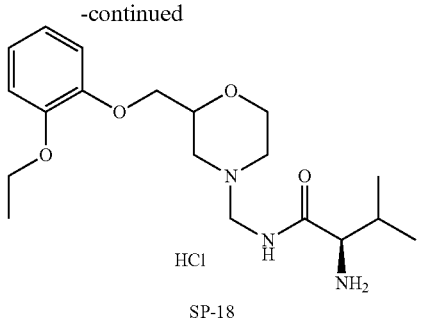

SP-18

Solution of SP-18A (70 mg, 0.15 mmol) and 2M HCl in dioxane was stirred at room temperature overnight. The solvent was evaporated and dried under vacuum to obtain 50 mg (76%) of pure desired product (SP-18) as a brown solid. LCMS: M+H=366.20. Purity 98.73% by ELS detector. $^1$H NMR (CDCl$_3$, 400 MHz): δ ppm 9.8-10.5 (br m, 1H), 8.2-8.5 (br s, 2H), 6.75-7.1 (m, 4H), 4.2-5.0 (m, 4H), 3.9-4.2 (m, 6H), 3.70-3.87 (m, 2H), 3.0-3.5 (br s, 1H), 1.75-2.25 (m, 4H), 1.3-1.5 (m, 3H), 1.1 (br s, 6H).

SP-19: Pyridin-2-yl 2-((2-ethoxyphenoxy)methyl)morpholine-4-carboxylate

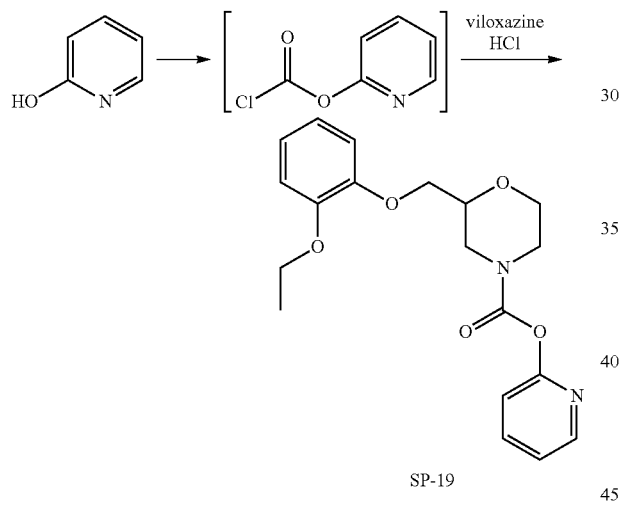

SP-19

A solution of triphosgene (163 mg, 0.55 mmol) in dichloromethane (DCM; 1 ml) was stirred in an ice bath at 0-5° C. temperature for 15 min and a solution of 2-hydroxypyridine (150 mg, 1.58 mmol), N,N-diisopropylethylamine (DIPEA; 208 mg, 1.61 mmol) in DCM (1 ml) was added dropwise. The reaction mixture allowed to attain room temperature. The completion of the reaction was monitored by TLC. After the reaction was completed, the reaction mixture was evaporated, reconstituted with DCM and evaporated (×3) to remove excess of triphosgene. Residue was reconstituted with DCM, and a solution of 2-((2-ethoxyphenoxy)methyl) morpholine hydrochloride (363 mg, 1.26 mmol) and TEA (13.6 mg, 1.34 mmol) in DCM added and stirred overnight at room temperature. The reaction mixture was absorbed on silica and was purified by column chromatography using hexane-ethyl acetate (2:1) to obtain the target compound (SP-19) as a semisolid 56 mg (12.3%). LCMS: M+H=359.08. Purity 100% by ELS detector. $^1$H NMR (400 MHz, CDCL$_3$): δ 1.25-1.46 (m, 3H), 3.02-3.34 (m, 2H), 3.69-3.76 (m, 1H), 3.95-4.16 (m, 7H), 4.28-4.42 (d, 1H), 6.85-6.99 (m, 4H), 7.11 (dd, 1H), 7.21 (dd, 1H), 7.75-7.83 (m, 1H), 8.39 (dd, 1H).

SP-20: 2-Chloropyridin-4-yl 2-((2-ethoxyphenoxy) methyl)morpholine-4-carboxylate.

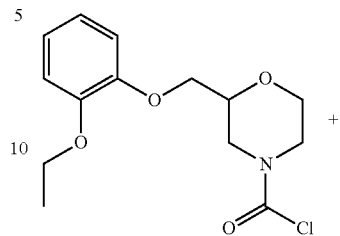

Intermediate 1

SP-20

To a stirred and ice-cooled solution of 2-chloro-4-hydroxy pyridine, (95 mg, 0.73 mmol) in anhydrous THF (10 mL) was added 2-((2-ethoxyphenoxy)methyl)morpholine-4-carbonyl chloride (Intermediate 1) (273 mg, 0.33 mmol), followed by a dropwise addition of NaH (60% in oil, 35 mg, 0.146 mmol). The reaction mixture was stirred for 14 hours at room temperature under argon. After evaporation of the solvent in vacuo, water (5 mL) was added and extracted with ether (3×10 mL). The organic phase was washed with dilute NaOH (pH 10-11), dried, and evaporated to dryness in vacuum. Purification by column chromatography (hexane: EtOAc 2:1) afforded 83 mg (29%) of a semisolid (SP-20). LCMS: Purity 100% by ELS detector. MS: M+H=393.08. $^1$H NMR (CDCl$_3$, 400 MHz): δ ppm 1.38-1.47 (m, 3H), 3.04-3.32 (m, 2H), 3.70 (t, 1H) 3.9-3.93 (m, 1H), 4.03-4.08 (m, 5H), 4.15-4.18 (m, 1H), 4.30-4.35 (m, 1H), 6.87-6.99 (m, 4H), 7.11-7.12 (m, 1H), 7.23 (d, 1H), 8.37 (d, 1H).

SP-21: Methylene bis(2-((2-ethoxyphenoxy)methyl)morpholine-4-carboxylate).

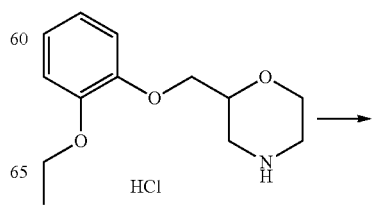

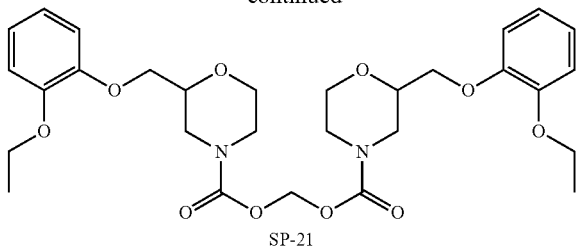

SP-21

A solution of 2-((2-ethoxyphenoxy)methyl)morpholine hydrochloride (108 mg, 0.4 mmol) and methylene dibromide (50 mg) in DMF (2 ml) was added a slurry of cesium carbonate (100 mg, 1.2 mmol). Carbon dioxide gas was passed into the reaction for 30 minutes and the mixture stirred at room temperature for 48 hours. The reaction mass was filtered and the filtrate was concentrated under vacuum. The residue was dissolved in chloroform and purified by column chromatography (hexane:EtOAc 4:1) to afford 52 mg (22.6%) of a solid. Purity 100% by ELS detector. MS: M+H=575.15. $^1$H NMR (CDCl$_3$, 400 MHz): δ ppm 6.7-7.00 (m, 8H), 5.83 (s, 2H), 3.8-4.2 (m, 16H), 3.5-3.6 (m, 2H), 2.8-3.0 (m, 4H), 1.43-1.47 (t, 6H).

SP-22: 1-((L-phenylalanyl)oxy)ethyl 2-((2-ethoxyphenoxy)methyl)morpholine-4-carboxylate.

Step 1.

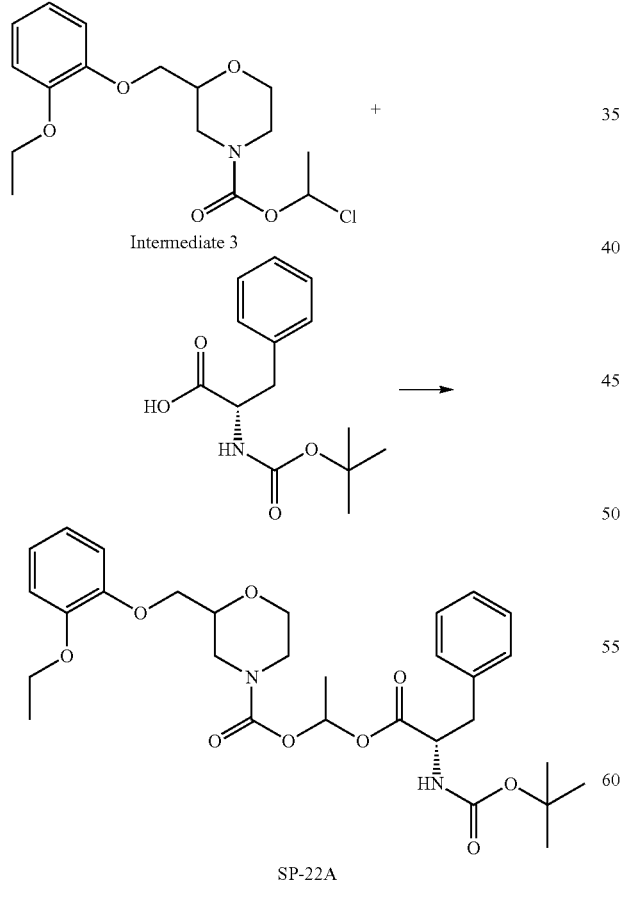

A reaction mixture of N-Boc-phenylalanine (175 mg, 0.66 mmol), cesium carbonate (107 mg, 0.33 mmol), in methanol (1.3 ml) were stirred at room temperature for 3 hours, then methanol was evaporated, residue reconstituted with DMF (1 ml). To the reaction mixture was added 1-chloroethyl 2-((2-ethoxyphenoxy)methyl)morpholine-4-carboxylate (Intermediate 3) (150 mg, 0.42 mmol). The resulting mixture was stirred at 80° C. for 20 hours. The DMF was then evaporated under vacuum, the residue dissolved in chloroform, and then purified by column chromatography (hexane:EtOAc 8:2) to afford 232 mg (61%) of semi-solid oil.

Step 2:

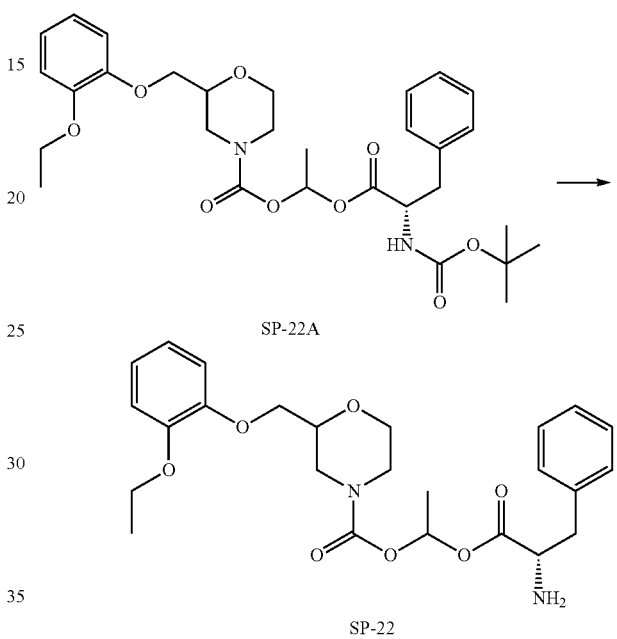

Solution of SP-22A (140 mg, 0.238 mmol) and 2M HCl in dioxane was stirred at room temperature overnight. The solvent was evaporated and dried under vacuum to obtain 58 mg (52%) of pure desired product as a light brown solid. LCMS: Purity: 100% by ELS detector. MS: M+H=495.24. $^1$H NMR (CDCl$_3$, 400 MHz): δ ppm 1.25-1.50 (m, 6H), 2.95-3.06 (m, 2H), 3.35-3.71 (m, 4H) 3.76-4.13 (m, 8H) 4.34-4.40 (m, 2H) 6.85-6.92 (m, 5H), 7.25-7.36 (m, 5H), 8.70 (br. s., 1H), 8.79 (br. s., 1H).

SP-23 1-((dimethyl-L-valyl)oxy)ethyl 2-((2-ethoxyphenoxy)methyl)morpholine-4-carboxylate, hydrochloride.

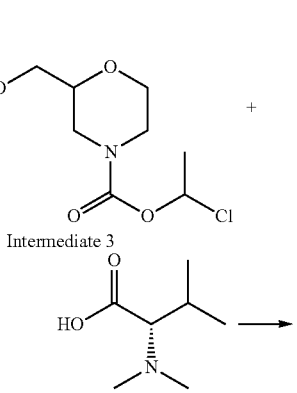

-continued

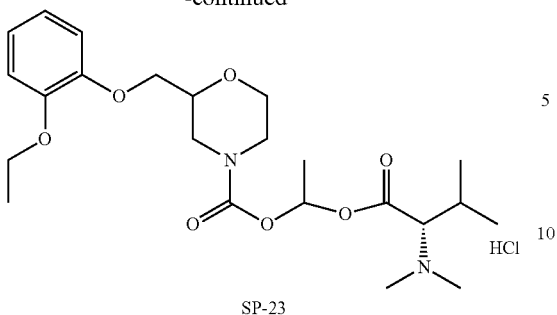

SP-23

A reaction mixture of L-Val-N,N-dimethyl (100 mg, 0.68 mmol), cesium carbonate (110 mg, 0.34 mmol), in methanol (0.75 ml) were stirred at room temperature for 3 hours, then methanol evaporated, residue reconstituted with DMF (1 ml). To the reaction mixture was added 1-chloroethyl 2-((2-ethoxyphenoxy)methyl)morpholine-4-carboxylate (Intermediate 3) (160 mg, 0.44 mmol). The resulting mixture was stirred at 80° C. for 20 hours.

The DMF was evaporated under vacuum, residue dissolved in chloroform and purified by column chromatography (hexane:EtOAc 3:2) to afford 91 mg (45.7%) of semi-solid.

77 mg of the parent compound was dissolved in 2 ml of chloroform and 0.17 ml of 2M HCl in dioxane was added. The reaction mixture was stirred at room temperature for 2 hours. The solvent was then evaporated under Argon and then under vacuum to obtain 81 mg of an oil. LCMS: Purity: 99.61% by ELS detector. MS: M+H=453.30 M+Na=475.28. $^1$H NMR (CDCl$_3$, 400 MHz): δ ppm 0.89 (dd, 3H), 0.97 (d, 3H), 1.45 (t, 3H), 1.53 (d, 3H), 1.63 (s, 1H), 2.01 (dt, 6.54 Hz, 1H), 2.31 (s, 6H), 2.72 (m, 1H), 3.04 (br. s, 2H), 3.59 (d, 1H), 3.81-4.18 (m, 8H), 6.88-6.91 (m, 5H).

SP-24: 1-((Acetyl-L-valyl)oxy)ethyl 2-((2-ethoxyphenoxy)methyl)morpholine-4-carboxylate.

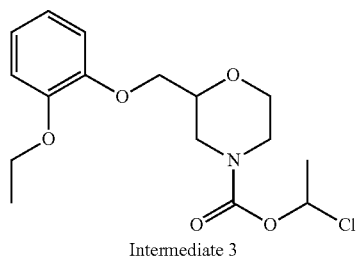

Intermediate 3

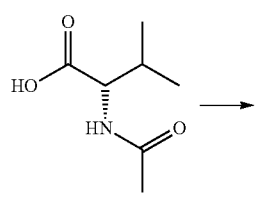

-continued

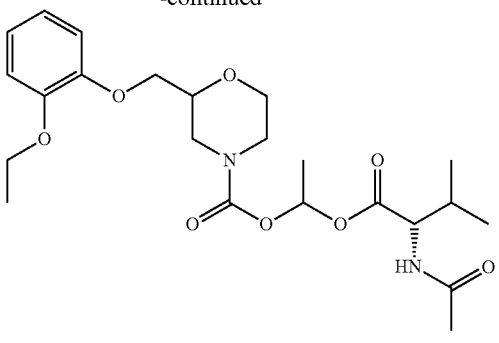

SP-24

A reaction mixture of N-acetylvaline (120 mg, 0.69 mmol), cesium carbonate (110 mg, 0.34 mmol), in methanol (0.9 ml) were stirred at room temperature for 3 hours, then methanol evaporated, residue reconstituted with DMF (1 ml). To the reaction mixture was added 1-chloroethyl 2-((2-ethoxyphenoxy)methyl)morpholine-4-carboxylate (Intermediate 3) (160 mg, 0.44 mmol). The resulting mixture was stirred at 80° C. for 20 hours. The DMF was evaporated under vacuum, residue dissolved in chloroform and purified by column chromatography (hexane:EtOAc 3:2) to afford 75 mg (37%) of oil. LCMS: Purity: 100% by ELS detector. MS: M+H=473.26 M+Na=495.24. $^1$H NMR (CDCl$_3$, 400 MHz): δ ppm 0.82-1.03 (m, 3H), 0.93 (d, 3H), 1.45 (br. s., 3H), 1.52-1.53 (m, 3H), 2.04 (d, 3H), 2.17 (m, 1H), 2.94-3.10 (m, 2H), 3.57-3.60 (m, 1H), 3.84-4.17 (m, 8H), 4.55-4.62 (m, 1H), 5.97 (br. s., 1H), 6.89-6.95 (m, 5H).

SP-25: 1-((methyl-D-valyl)oxy)ethyl 2-((2-ethoxyphenoxy)methyl)morpholine-4-carboxylate, trifluoroacetic acid salt.

Step 1.

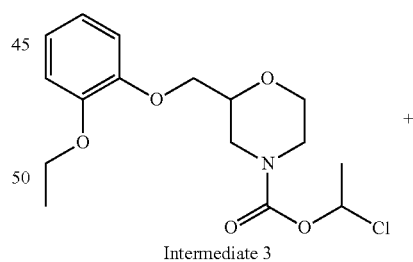

Intermediate 3

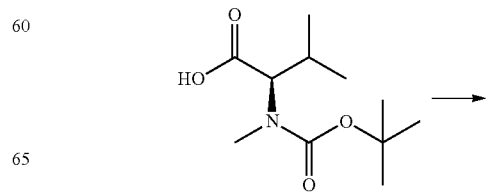

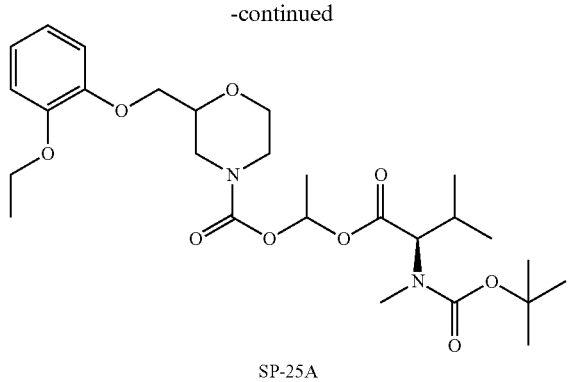

SP-25A

A reaction mixture of N-Boc-D-Valine (160 mg, 0.69 mmol), cesium carbonate (110 mg, 0.35 mmol), in methanol (1.2 ml) was stirred at room temperature for 3 hours, then methanol evaporated, residue reconstituted with DMF (1 ml). To the reaction mixture was added 1-chloroethyl 2-((2-ethoxyphenoxy)methyl)morpholine-4-carboxylate (Intermediate 3) (160 mg, 0.44 mmol). The resulting mixture was stirred at 80° C. for 20 hours. DMF was evaporated under vacuum, residue dissolved in chloroform and purified by column chromatography (hexane:EtOAc 2:1) to afford 90 mg (36.1%) of semi-solid oil.

Step 2:

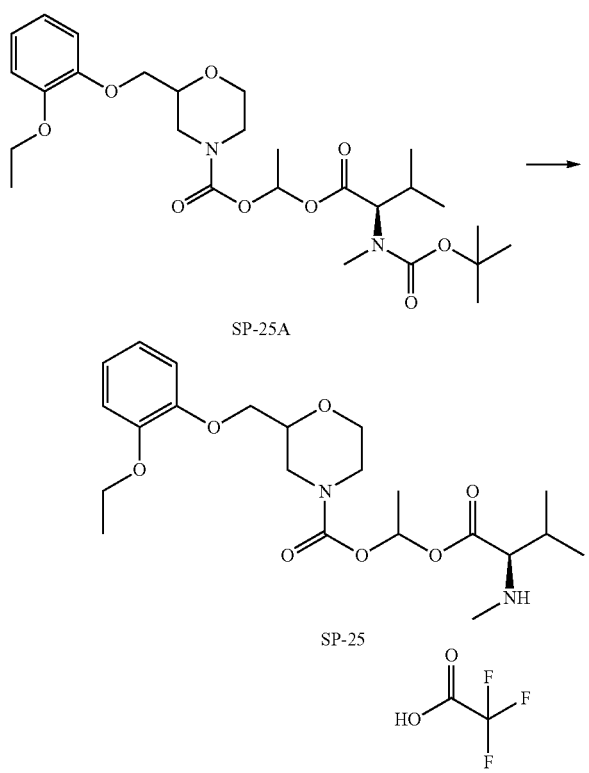

Solution of SP-25A (50 mg, 0.09 mmol) in DCM (1 ml) and TFA (0.1 ml) was stirred at room temperature overnight (18 hours). The solvent was then evaporated and dried under vacuum to obtain 35.8 mg (85.3%) of pure desired product as a yellow oil. LCMS: Purity: 100% by ELS detector. MS: M+H=439.24 $^1$H NMR (CDCl$_3$, 400 MHz): δ 0.98-1.15 (m, 6H), 1.36-1.49 (m, 3H), 1.57 (d, 3H), 2.37 (br. s., 1H), 2.78 (s, 3H), 2.88-3.10 (m, 2H), 3.14 (d, 1H), 3.49-3.64 (m, 1H), 3.67 (br. s., 1H), 3.84 (br. s., 1H), 3.89 (br. s., 1H), 3.97 (br. s., 2H), 4.00-4.11 (m, 3H), 4.16 (d, 2H), 6.84-7.00 (m, 5H).

SP-26: 1-((D-valyl)oxy)-2-methylpropyl 2-((2-ethoxyphenoxy)methyl)-morpholine-4-carboxylate HCl salt.

Step 1:

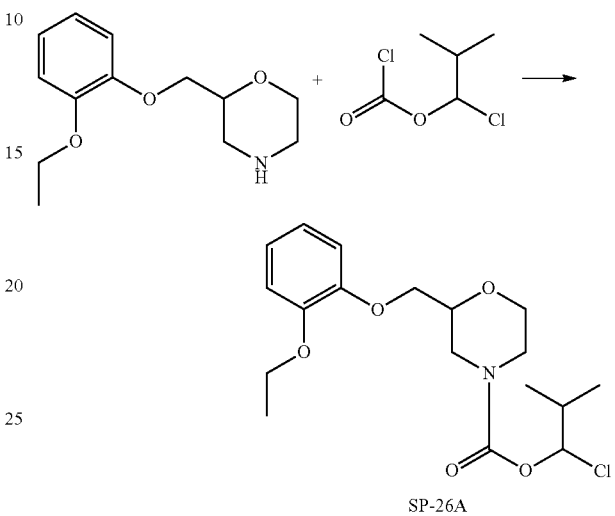

To a stirred ice cold mixture of 2-((2-ethoxyphenoxy)-methyl)morpholine hydrochloride (350 mg, 1.22 mmol), trimethylamine (271 mg, 2.68 mmol) dichloromethane was added dropwise 1-chloro-2-methylpropylchloroformate (210 mg, 1.46 mmol). The reaction mixture was stirred at 10-15° C. and allowed to attain room temperature and stirred for 2 hours. Precipitated solids were filtered and the filtrate was concentrated. The crude product was purified by column chromatography (hexane:EtOAc 4:1) to afford 0.55 gm (59.3%) of oil. $^1$H NMR (CDCl$_3$, 400 MHz): δ ppm 1.06-1.09 (m, 6H), 1.43-1.46 (t, 3H), 2.18-2.22 (m, 1H), 2.95-3.20 (m, 2H), 3.55-3.69 (m, 1H), 3.86-4.27 (m, 8H), 6.36-6.37 (d, 1H), 6.86-6.97 (m, 4H).

Step 2.

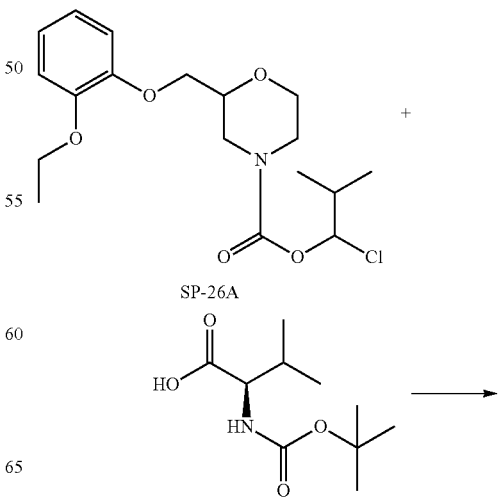

-continued

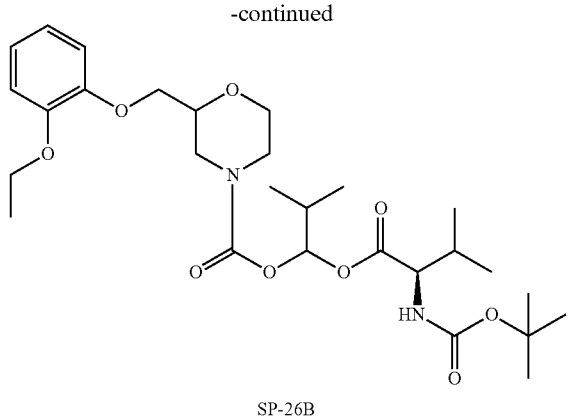

SP-26B

A reaction mixture of N-Boc-D-Valine (200 mg, 0.92 mmol), cesium carbonate (150 mg, 0.46 mmol), in methanol (1.5 ml) were stirred at room temperature for 2 hours, then methanol evaporated, residue reconstituted with DMF (1 ml). To the reaction mixture was added 1-chloro-2-methylpropyl 2-((2-ethoxyphenoxy)methyl)morpholine-4-carboxylate (SP-26A) (230 mg, 0.59 mmol). The resulting mixture was stirred at 80° C. for 20 hours. DMF was evaporated under vacuum, residue dissolved in chloroform and purified by column chromatography (hexane:EtOAc 4:1) to afford 170 mg (52.1%) of semisolid oil.

Step 3:

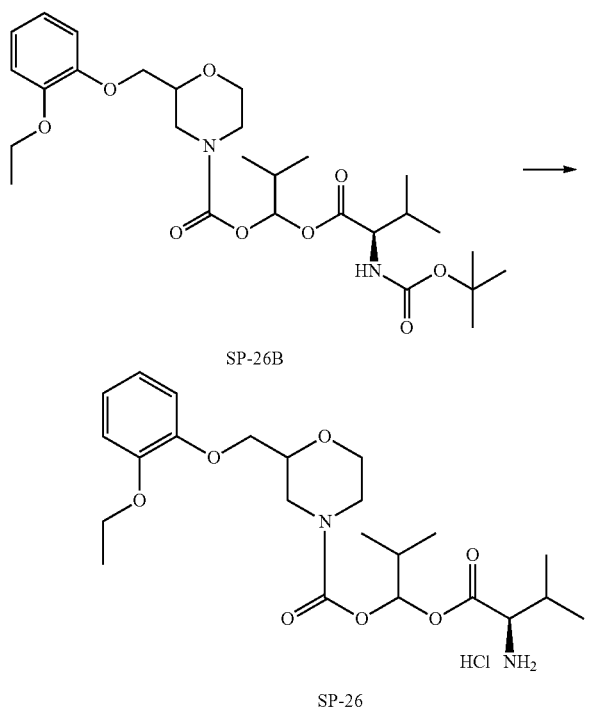

Solution of SP-26B (110 mg, 0.2 mmol) in dioxane (1 ml) and 2M HCl in dioxane (0.4 ml) stirred at room temperature overnight (18 hours). The solvent was then evaporated and dried under vacuum to obtain 80 mg (88%) of pure desired product as an oil. LCMS: Purity: 100% by ELS detector. MS: M+H=453.22. $^1$H NMR (CDCl$_3$, 400 MHz): δ ppm 0.92-1.04 (m, 6H), 1.04-1.23 (m, 6H), 1.42 (t, 3H), 2.09 (br, 1H), 2.48 (br, 1H), 2.89-3.17 (m, 1H), 3.49-4.25 (m, 13H), 6.81-6.73 (m, 1H), 6.88-6.92 (m, 4H), 8.70-8.76 (d, 2H).

SP-27: 1-(((R)-2-(aminomethyl)-3-methylbutanoyl)oxy) ethyl 2-((2-ethoxyphenoxy)methyl)morpholine-4-carboxylate trifluoroacetic acid salt.

Step 1.

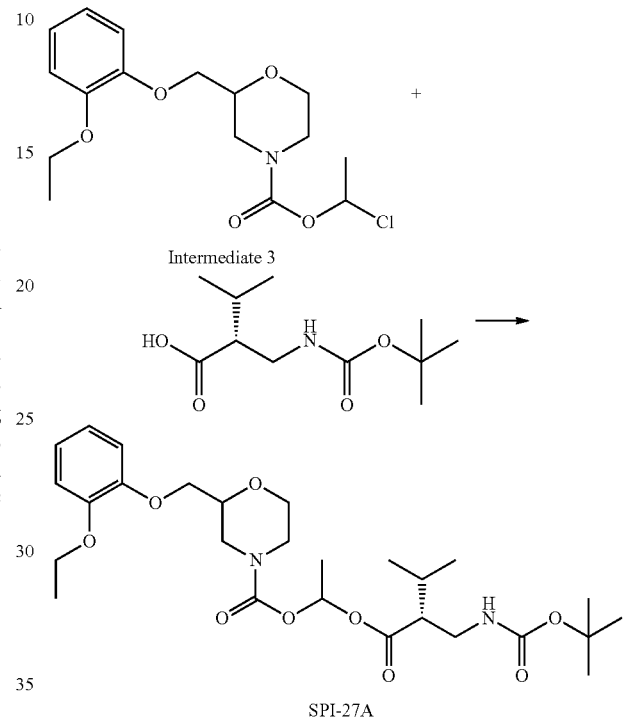

A reaction mixture of N-Boc-3-amino-2-isopropionic acid (100 mg, 0.43 mmol), cesium carbonate (70 mg, 0.22 mmol), in methanol (0.75 ml) were stirred at room temperature for 2 hours ("h"), then methanol evaporated, residue reconstituted with DMF (0.75 ml). To the reaction mixture was added chloromethyl 2 1-chloroethyl 2-((2-ethoxyphenoxy)methyl)morpholine-4-carboxylate (Intermediate 3) (99 mg, 0.28 mmol). The resulting mixture was stirred at 80° C. for 20 hours. The DMF was evaporated under vacuum, the residue dissolved in chloroform and purified by column chromatography (hexane:EtOAc 4:1) to afforded 117 mg (77.6%) of semi-solid.

Step 2:

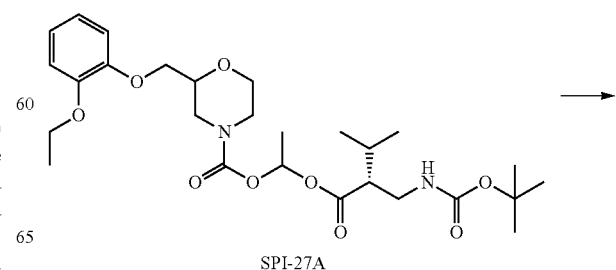

SPI-27A

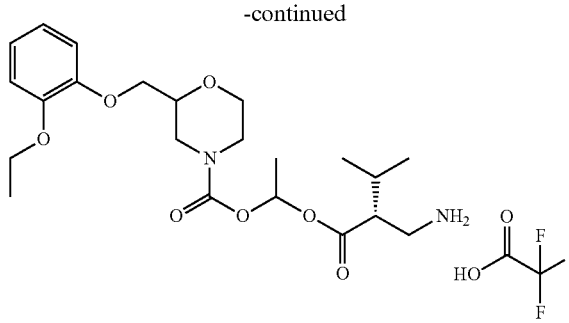

SP-27

A solution of SP-27A (58 mg, 0.012 mmol) in chloroform (1 ml) and TFA (0.2 ml) stirred at room temperature for 24 hours. The solvent was then evaporated and dried under vacuum to obtain 52 mg (90%) of pure desired product as oil. LCMS: Purity: 100% by ELS detector. MS: M+H=439.21. $^1$H NMR (CDCl$_3$, 400 MHz): δ ppm 0.86-1.04 (m, 6H), 1.35-1.49 (m, 3H), 1.53 (br. s., 3H), 2.96-3.09 (m, 1H), 3.10-3.31 (m, 2H), 3.79-3.91 (m, 2H), 3.92-4.16 (m, 6H), 6.85-7.01 (m, 4H), 7.65 (br. s., 3H).

SP-28: 1-(((R)-2-(aminomethyl)-3-methylbutanoyl)oxy) ethyl 2-((2-ethoxyphenoxy)methyl)morpholine-4-carboxylate trifluoroacetic acid salt.

Step 1.

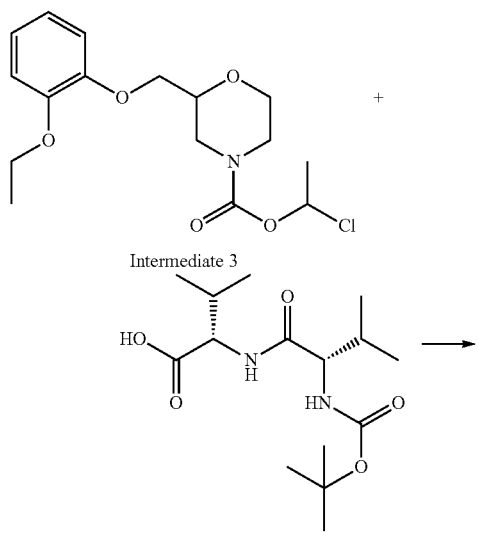

A reaction mixture of Boc-Val-Val (150 mg, 0.47 mmol), cesium carbonate (80 mg, 0.24 mmol), in methanol (1.13 ml) was stirred at room temperature for 2 hours, then methanol evaporated, residue reconstituted with DMF (1 ml). To the reaction mixture was added 1-chloroethyl 2-((2-ethoxyphenoxy)methyl)morpholine-4-carboxylate (Intermediate 3) (110 mg, 0.3 mmol). The resulting mixture was stirred at 80° C. for 18 hours. The DMF was evaporated under vacuum, residue dissolved in DCM and purified by column chromatography (hexane:EtOAc 1:1) to afforded 35 mg (11.9%) of semi-solid.

Step 2:

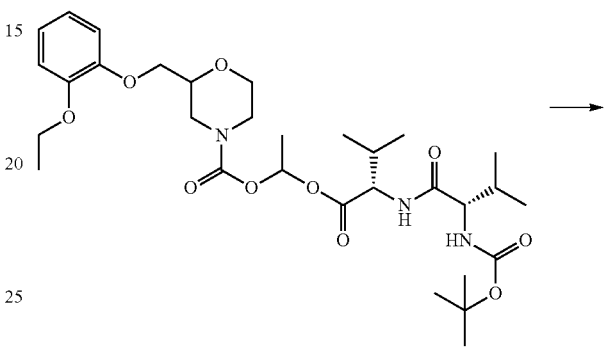

SP-28A

SP-28

Solution of SP-28A (32 mg, 0.005 mmol) in chloroform (1 ml) and TFA (0.085 ml) was stirred at room temperature for 6 hours. The solvent was then evaporated and dried under vacuum to obtain 33 mg (98%) of pure desired product as yellow semi-solid. LCMS: Purity: 100% by ELS detector. MS: M+H=524.27. $^1$H NMR (CDCl$_3$, 400 MHz): δ ppm 0.87-1.16 (m, 11H), 1.36-1.56 (m, 6H), 2.18 (br. s., 2H), 2.99-3.05 (m, 2H), 3.59-4.24 (m, 11H), 6.18 (br. s., 2H), 6.84-7.05 (m, 5H), 7.34-7.53 (m, 1H), 8.10 (br. s., 2H).

SP-29: (((R)-3-amino-4-methylpentanoyl)oxy)methyl 2-((2-ethoxyphenoxy)-methyl)morpholine-4-carboxylate, trifluoroacetic acid salt Step 1.

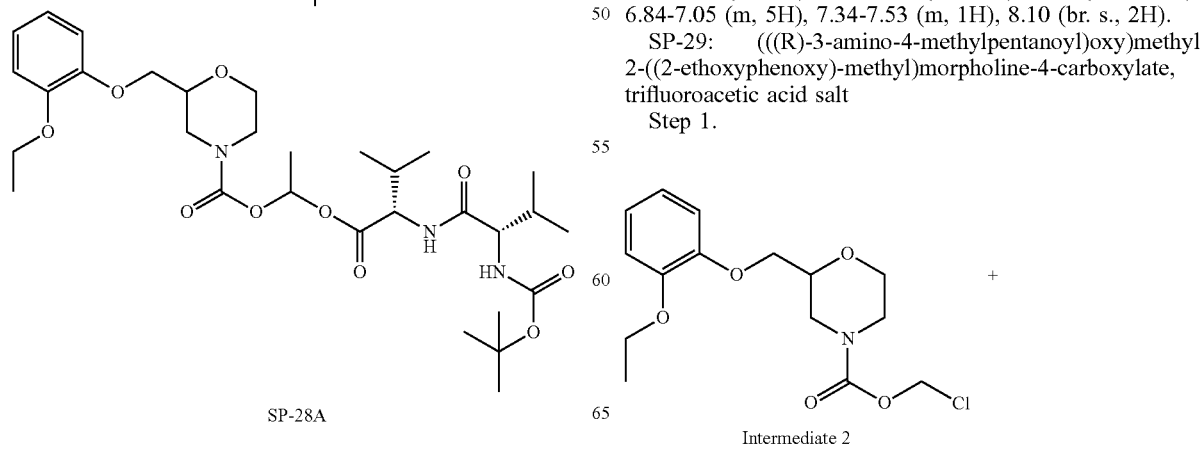

Intermediate 2

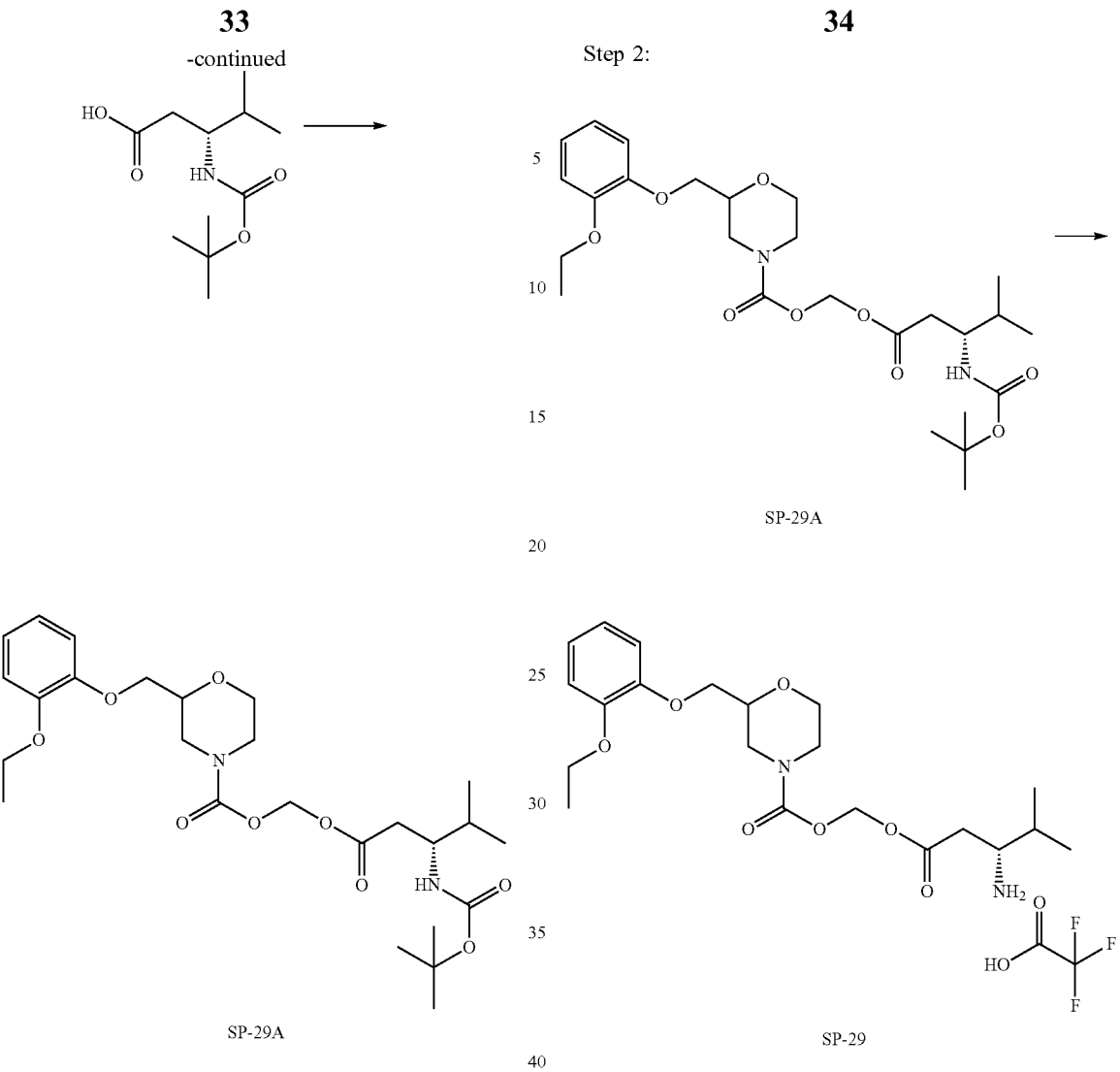

SP-29A

SP-29

A reaction mixture of Boc-L-O-leucine (150 mg, 0.65 mmol), cesium carbonate (110 mg, 0.146 mmol), in methanol (1.13 ml) was stirred at room temperature for 2 hours, then methanol evaporated, residue reconstituted with DMF (1 ml). To the reaction mixture was added chloromethyl 2-((2-ethoxyphenoxy)methyl)morpholine-4-carboxylate (Intermediate 2) (140 mg, 0.42 mmol). The resulting mixture was stirred at 80° C. for 18 hours. The DMF was evaporated under vacuum, residue dissolved in DCM and purified by column chromatography (hexane:EtOAc 4:1) to afford 120 mg (54.5%) of semi-solid.

Solution of SP-29A (58 mg, 0.11 mmol) in chloroform (1 ml) and TFA (0.55 ml) stirred at room temperature for 24 hours. The solvent was then evaporated and dried under vacuum to obtain 50 mg (90%) of pure desired product as oil. LCMS: Purity: 100% by ELS detector. MS: M+H=425.19. $^1$H NMR (CDCl$_3$, 400 MHz): δ ppm 1.03 (dd, 6H), 1.36-1.48 (m, 3H), 2.04 (m, 1H), 2.79 (d, 2H), 2.93-3.22 (m, 2H), 3.46 (br. s. 1H), 3.57-3.65 (m, 1H), 3.90-4.18 (m, 6H), 5.72-5.91 (m, 2H), 6.86-7.02 (m, 3H), 7.43-7.73 (m, 3H), 8.35 (br. s., 3H).

SP-30: Bis(((2-((2-ethoxyphenoxy)methyl)morpholine-4-carbonyl)oxy)methyl) pyridine-3,5-dicarboxylate

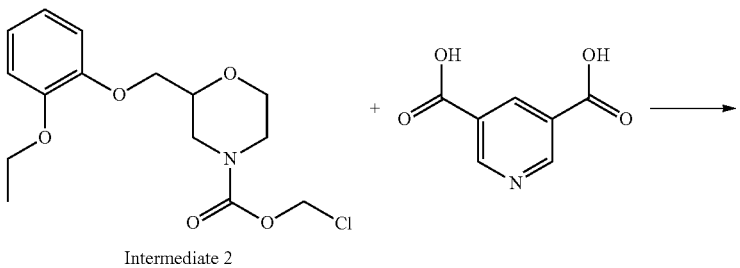

Intermediate 2

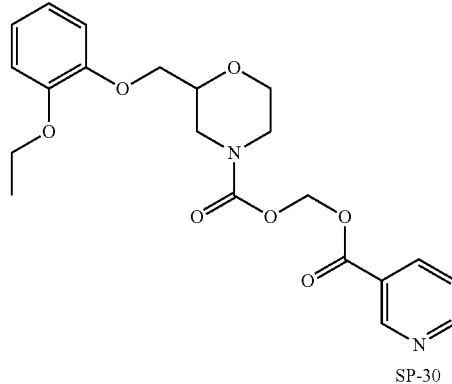

SP-30

A reaction mixture of 3,5-pyridinedicarboxylic acid (75 mg, 0.4 mmol), cesium carbonate (190 mg, 0.6 mmol), in methanol (0.6 ml) was stirred at room temperature for 2 hours, then methanol evaporated, residue reconstituted with DMF (1 ml). To the reaction mixture was added chloromethyl 2-((2-ethoxyphenoxy)methyl)morpholine-4-carboxylate (Intermediate 2) (370 mg, 1.1 mmol). The resulting mixture was stirred at 80° C. for 18 hours. DMF was evaporated under vacuum, residue dissolved in DCM and purified by column chromatography (hexane:EtOAc 1:1) to afford 56 mg (18.5%) of semi-solid oil. LCMS: Purity: 100% by ELS detector. MS: M+H=754.21. ¹H NMR (CDCl₃, 400 MHz): δ ppm 1.44 (t, 6H), 2.92-3.21 (m, 4H), 3.57-3.67 (m, 2H), 3.84 (br. s, 2H) 3.93-4.12 (m, 12H), 4.18-4.27 (m, 2H), 6.07-6.11 (m, 4H), 6.82-7.04 (m, 8H), 8.93 (s, 1H), 9.43 (s, 2H).

SP-31: ((2,2'-(methylazanediyl)bis(acetyl))bis(oxy))bis(methylene) bis(2-((2-ethoxyphenoxy)methyl)morpholine-4-carboxylate).

A reaction mixture of methyliminodiacetic acid (50 mg, 0.3 mmol), cesium carbonate (144 mg, 0.4 mmol), in methanol (0.4 ml) was stirred at room temperature for 2 hours, then methanol evaporated, residue reconstituted with DMF (1 ml). To the reaction mixture was added chloromethyl 2-((2-ethoxyphenoxy)methyl)morpholine-4-carboxylate (Intermediate 2) (280 mg, 0.8 mmol). The resulting mixture was stirred at 80° C. for 18 hours. DMF was evaporated under vacuum, residue dissolved in DCM and purified by column chromatography (hexane:EtOAc 1:1). Resulting product re-purified by reverse phase $C_{18}$ column using acetonitrile and water gradient mixture to obtain 30.5 mg (13.8%) of pure semisolid-oil product. LCMS: Purity: 100% by ELS detector. MS: M+H=734.23. ¹H MNR (CDCl₃, 400 MHz): δ ppm 1.43-1.48 (t, 6H), 2.55 (s, 3H), 2.89-3.18 (m, 4H), 3.51-3.69 (m, 6H), 3.82-4.24 (m, 16H), 5.82 (s, 4H), 6.83-7.00 (m, 8H).

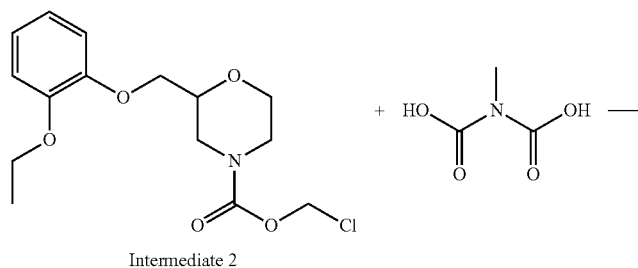

Intermediate 2

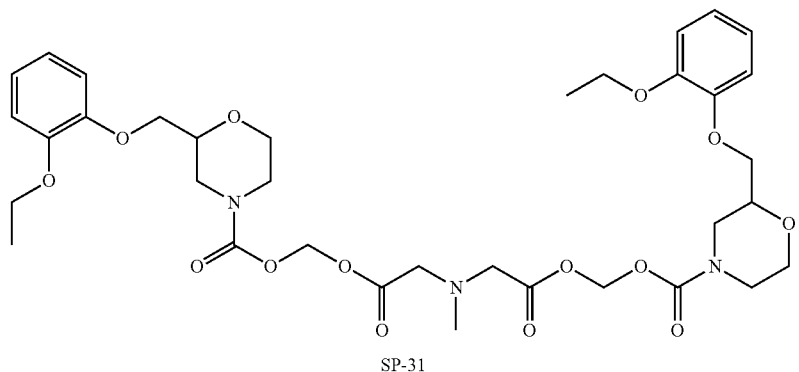

SP-31

SP-32: (((R)-2-(aminomethyl)-3-methylbutanoyl)oxy)methyl 2-((2-ethoxyphenoxy)methyl)morpholine-4-carboxylate, trifluoroacetic acid salt.

Step 1.

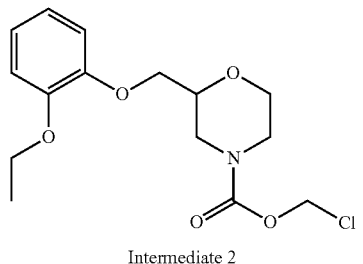

Intermediate 2

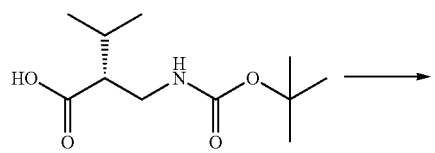

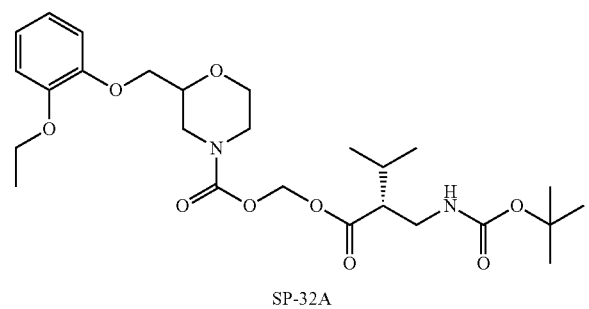

SP-32A

A reaction mixture of N-Boc-3-amino-2-isopropylpropionic acid (10 mg, 0.4 mmol), cesium carbonate (78 mg, 0.2 mmol), in methanol (0.85 ml) was stirred at room temperature for 2 hours, then methanol evaporated, residue reconstituted with DMF (1 ml). To the reaction mixture was added chloromethyl 2-((2-ethoxyphenoxy)methyl)morpholine-4-carboxylate (Intermediate 2) (95 mg, 0.3 mmol). The resulting mixture was stirred at 80° C. for 18 hours. The DMF was evaporated under vacuum, residue dissolved in DCM and purified by column chromatography (hexane:EtOAc 4:1) to afford 80 mg (50.8%) of semi-solid.

Step 2:

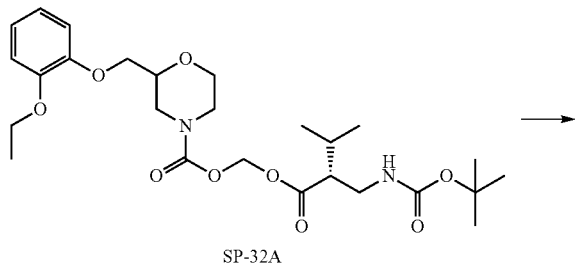

SP-32A

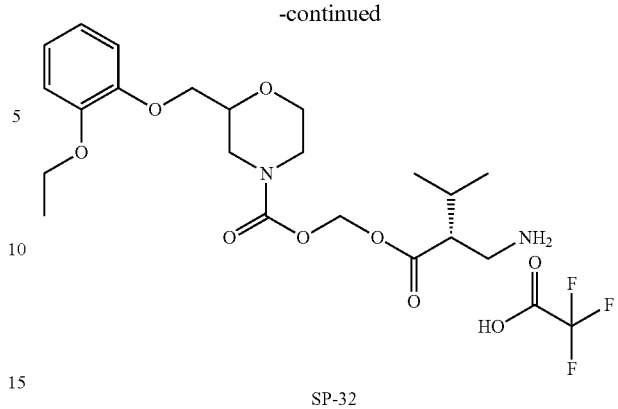

SP-32

Solution of SP-32A (65 mg, 0.124 mmol) in chloroform (1 ml) and TFA (0.23 ml) was stirred at room temperature for 24 hours. Solvent evaporated and dried under vacuum to obtain 49 mg (93%) of pure desired product as a semisolid-oil. LCMS: Purity: 100% by ELS detector. MS: M+H=425.18. $^1$H NMR (CDCl$_3$, 400 MHz): δ ppm 0.95 (d, 3H), 0.93 (d, 3H), 1.40-1.48 (m, 3H), 2.13 (br. s., 1H), 2.72-2.83 (m, 1H), 2.90-3.16 (m, 3H), 3.20-3.32 (m, 1H), 3.51-3.67 (m, 1H), 3.84 (d, 1H), 3.91-4.20 (m, 7H), 5.74-5.86 (m, 2H), 6.83-7.01 (m, 4H).

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

In an embodiment, a process for preparing 2-((2-ethoxyphenoxy)methyl)morpholine-4-carbonyl chloride (Intermediate 1) is provided, comprising:

reacting 2-((2-ethoxyphenoxy)methyl)-morpholine with a reaction mixture comprising triphosgene

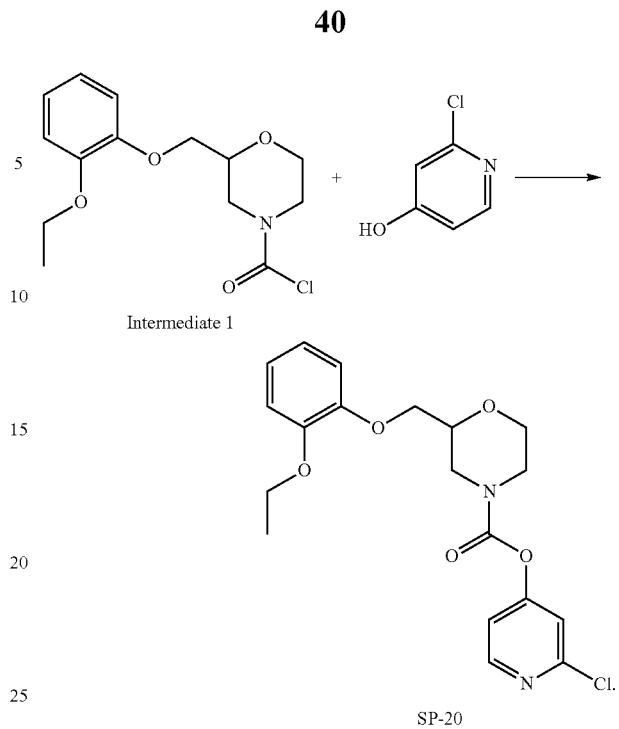

Intermediate 1

SP-20

In further embodiments, this reaction mixture further comprises anhydrous tetrahydrofuran.

In some embodiments, a process for preparing chloromethyl 2-((2-ethoxyphenoxy)methyl)morpholine-4-carboxylate (Intermediate 2) is provided, comprising:

reacting 2-((2-ethoxyphenoxy)methyl)-morpholine with a reaction mixture comprising 1-chloromethyl chloroformate

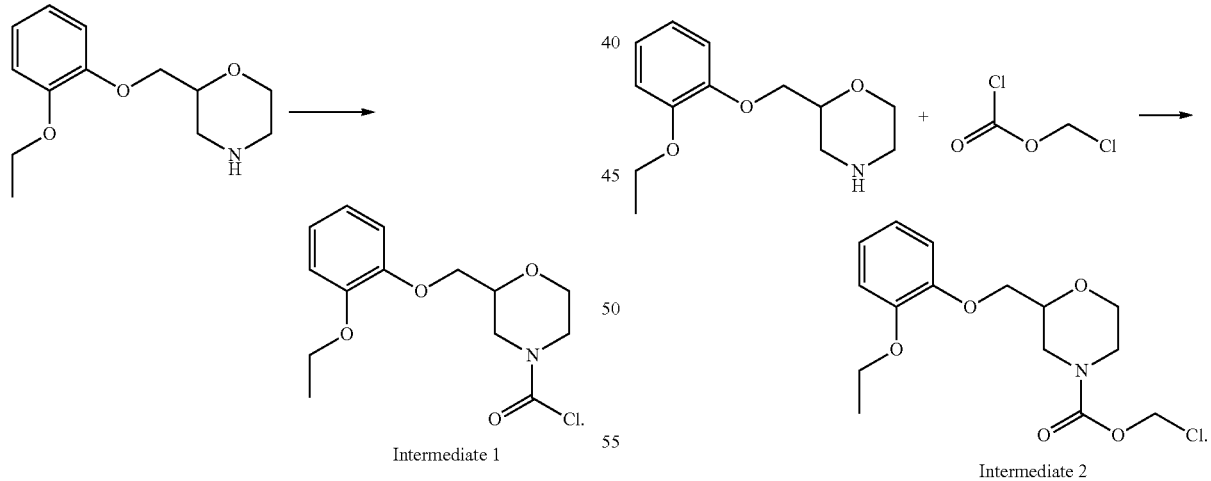

Intermediate 2

In further embodiments, the reaction mixture comprises dichloromethane. In other embodiments, the reaction mixture comprises sodium bicarbonate.

In some embodiments, Intermediate 1 is used to prepare 2-chloropyridin-4-yl 2-((2-ethoxyphenoxy)methyl)morpholine-4-carboxylate (SP-20), comprising:

reacting 2-((2-ethoxyphenoxy)methyl)morpholine-4-carbonyl chloride (Intermediate 1) and a reaction mixture comprising 2-chloro-4-hydroxy pyridine In further embodiments, this reaction mixture comprises trimethylamine. In other embodiments, this reaction mixture comprises dichloromethane.

In some embodiments, Intermediate 2 is used to prepare ((D-valyl)oxy)methyl 2-((2-ethoxyphenoxy)methyl)morpholine-4-carboxylate (SP-16), comprising:

(a) forming (SP-16A) by reacting Intermediate 2 with a reaction mixture comprising N-Boc-D-Valine; and

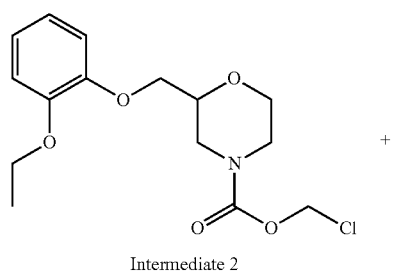

Intermediate 2

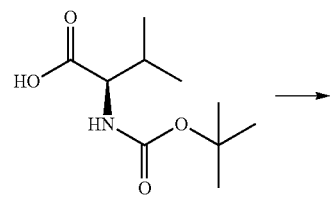

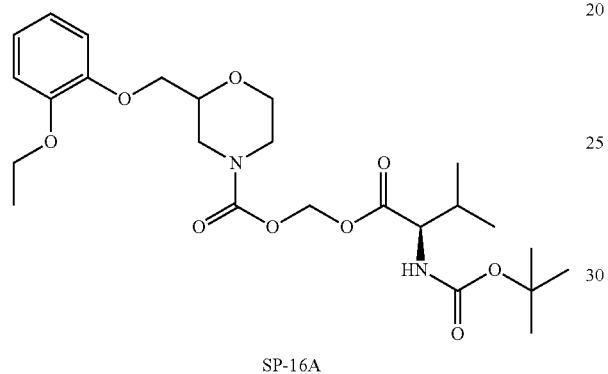

SP-16A (b) reacting SP-16A with dioxane in an organic acid

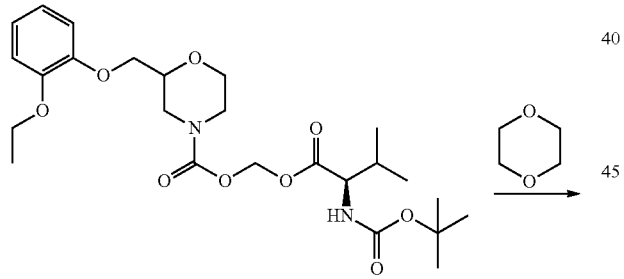

SP-16A

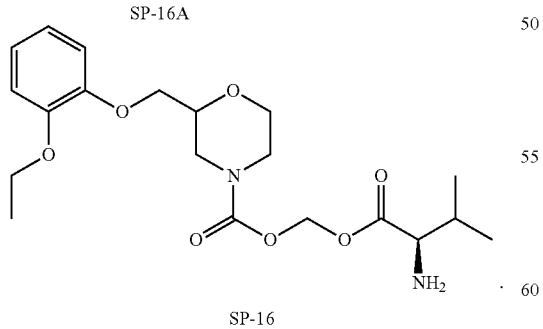

SP-16

In further embodiments, the reaction mixture comprises cesium carbonate. In other embodiments, the reaction mixture comprises methanol. In some embodiments, the organic acid is hydrochloric acid.

In some embodiments, Intermediate 2 is used to prepare (((R)-3-amino-4-methylpentanoyl)oxy)methyl 2-((2-ethoxyphenoxy)-methyl)morpholine-4-carboxylate (SP-29), comprising:

(a) forming SP-29A by reacting Intermediate 2 and a reaction mixture comprising Boc-L-β-leucine; and

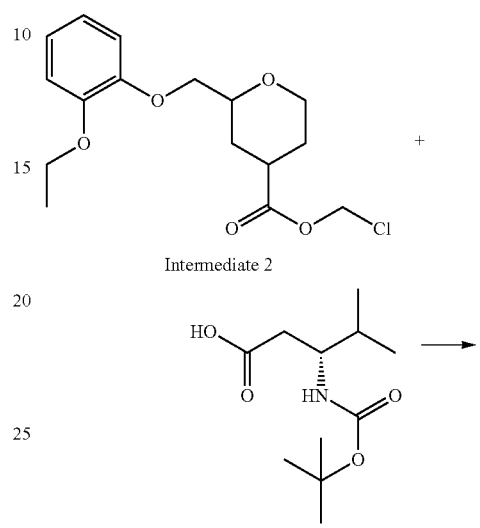

Intermediate 2

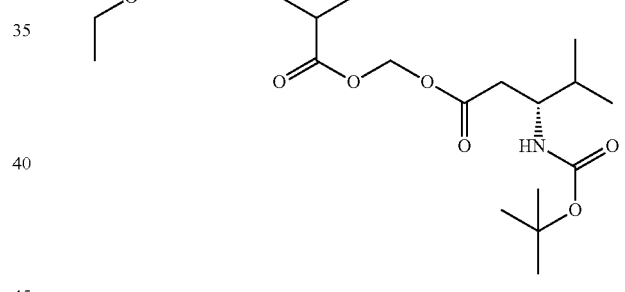

SP-29A (b) stirring SP-29A in chloroform and trifluoracetic acid

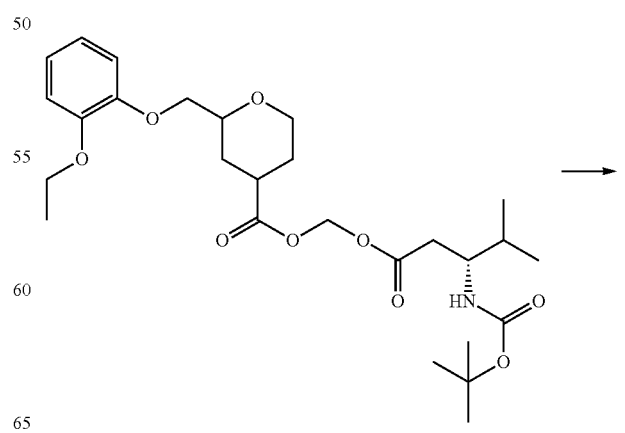

SP-29A

-continued

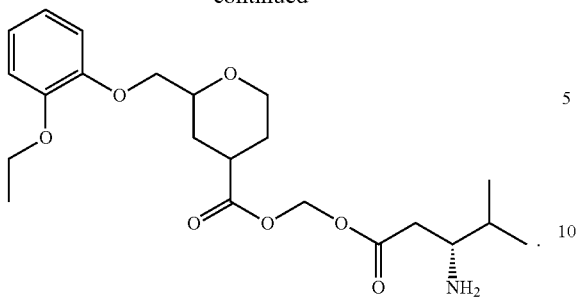

SP-29

In further embodiments, this reaction mixture comprises cesium carbonate. In other embodiments, the reaction mixture comprises methanol.

In other embodiments, Intermediate 2 is used to prepare bis(((2-((2-ethoxyphenoxy)methyl)morpholine-4-carbonyl)oxy)methyl)pyridine-3,5-dicarboxylate (SP-30), comprising:
  reacting Intermediate 2 and a reaction mixture comprising 3,5-pyridinedicarboxylic acid In further embodiments, this reaction mixture comprises cesium carbonate. In other embodiments, the reaction mixture comprises methanol.

In some embodiments, Intermediate 2 is used to prepare ((2-2'-(methylazanediyl)bis(acetyl))bis(oxy))bis(methylene) bis(2-((2-ethoxyphenoxy)methyl)morpholine-4-carboxylate) (SP-31), comprising:
  reacting chloromethyl 2-((2-ethoxyphenoxy)methyl)morpholine-4-carboxylate (Intermediate 2) and a reaction mixture comprising methyliminodiacetic acid

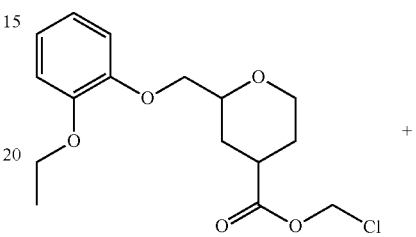

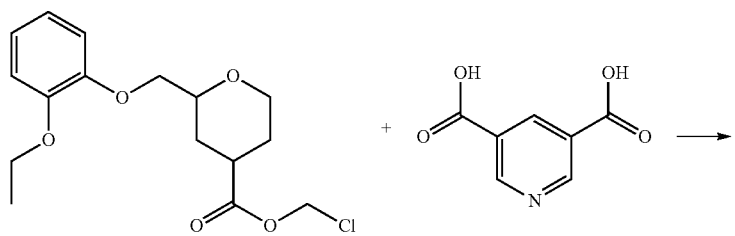

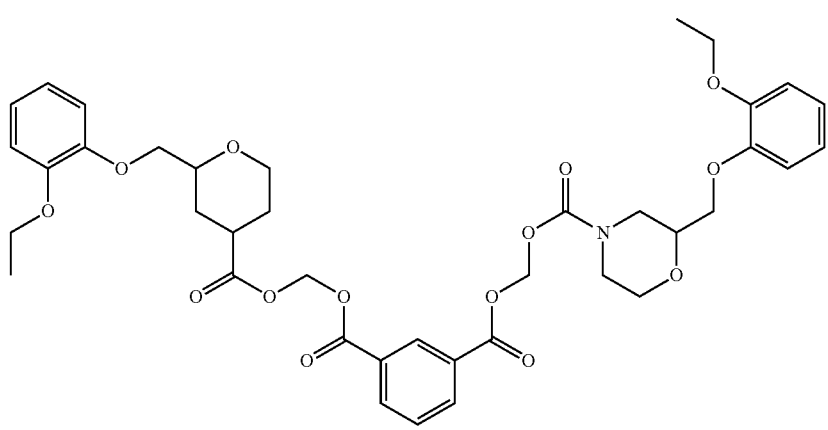

SP-30

-continued

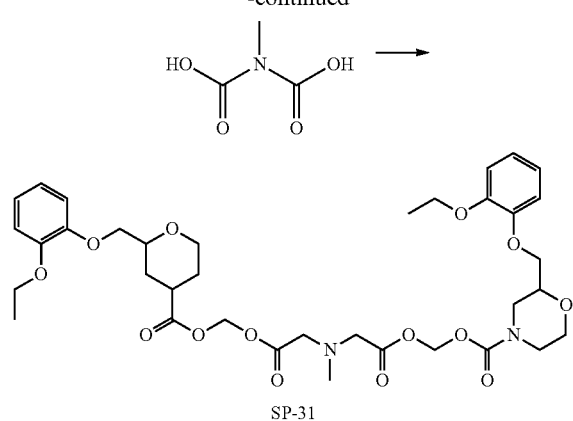

SP-31

In further embodiments, this reaction mixture comprises cesium carbonate. In other embodiments, the reaction mixture comprises methanol.

In other embodiments, Intermediate 2 is used to prepare (((R)-2-(aminomethyl)-3-methylbutanoyl)oxy)methyl 2-((2-ethoxyphenoxy)methyl)morpholine-4-carboxylate, trifluoroacetic acid salt (SP-32), comprising:

(a) forming SP-32A by reacting Intermediate 2 and a reaction mixture comprising N-Boc-3-amino-2-isopropylpropionic acid; and

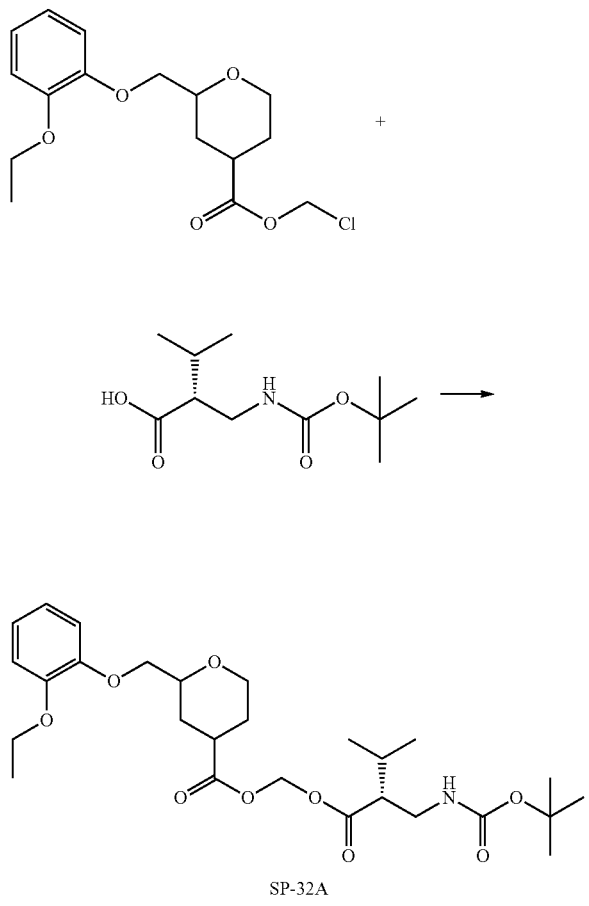

SP-32A (b) stirring SP-32A in chloroform and trifluoracetic acid

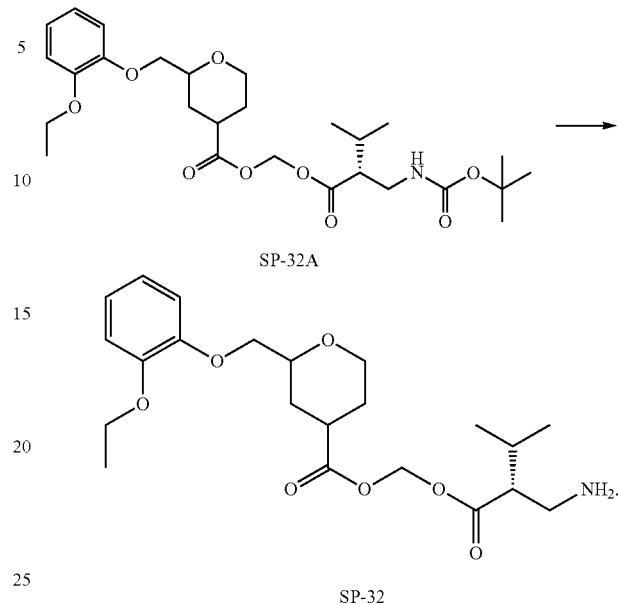

SP-32A

SP-32

In further embodiments, this reaction mixture comprises cesium carbonate. In other embodiments, the reaction mixture comprises methanol.

In another embodiment, a process for preparing 1-chloroethyl 2-((2-ethoxyphenoxy)methyl)morpholine-4-carboxylate (Intermediate 3) is provided, comprising:

reacting 2-((2-ethoxyphenoxy)methyl)morpholine with a reaction mixture comprising 1-chloroethyl chloroformate

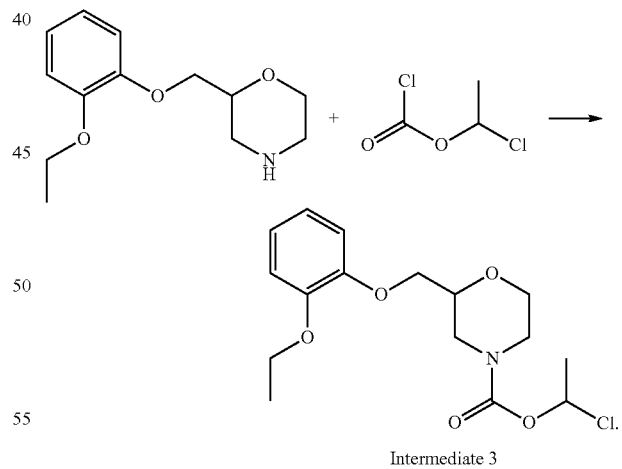

Intermediate 3

In further embodiments, this reaction mixture comprises trimethylamine. In other embodiments, the reaction mixture comprises dichloromethane.

In some embodiments, Intermediate 3 is used to prepare 1-((L-valyl)oxy)ethyl 2-((2-ethoxyphenoxy)methyl)morpholine-4-carboxylate (SP-17), comprising:

(a) forming SP-17A by reacting Intermediate 3 and a reaction mixture comprising N-Boc-L-Valine; and

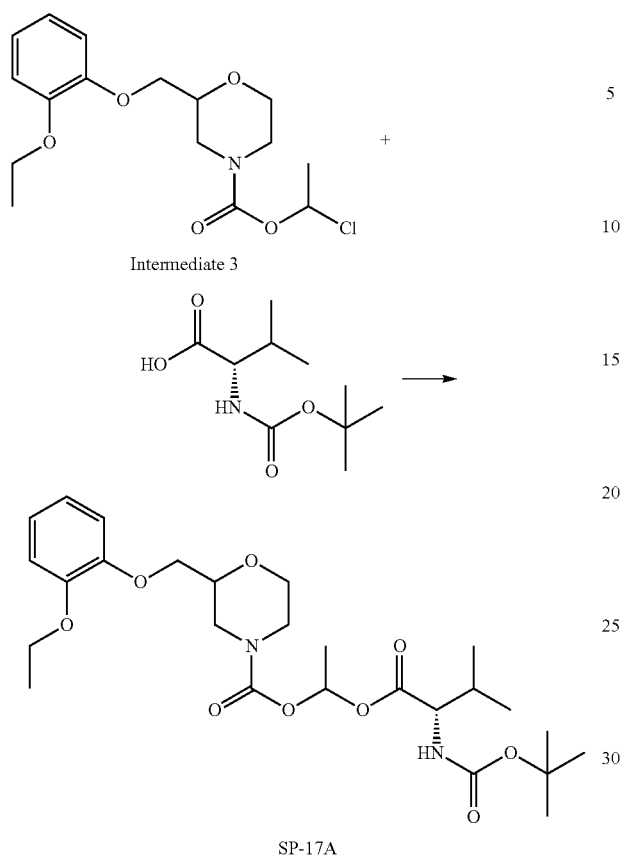

SP-17A (b) reacting SP-17A with dioxane in an organic acid

SP-17

In further embodiments, this reaction mixture comprises methanol. In other embodiments, the reaction mixture comprises cesium carbonate. In some further embodiments, the organic acid is hydrochloric acid.

In some embodiments, Intermediate 3 is used to prepare 1-((1-phenylalanyl)oxy)ethyl 2-((2-ethoxyphenoxy)methyl)morpholine-4-carboxylate (SP-22), comprising:

(a) forming SP-22A by reacting Intermediate 3 with a reaction mixture comprising N-Boc-phenylalanine; and

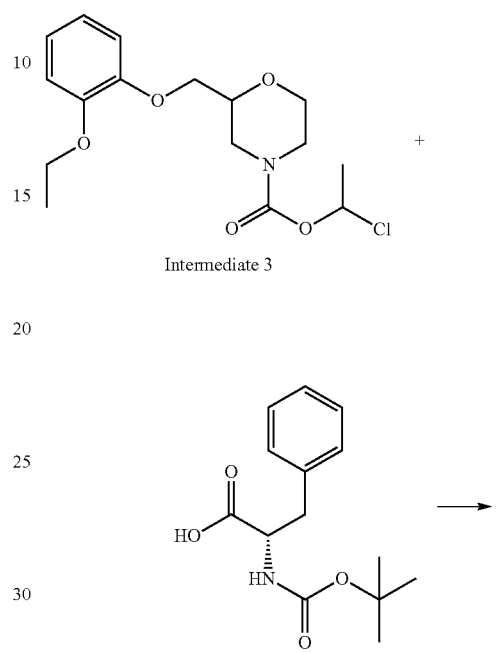

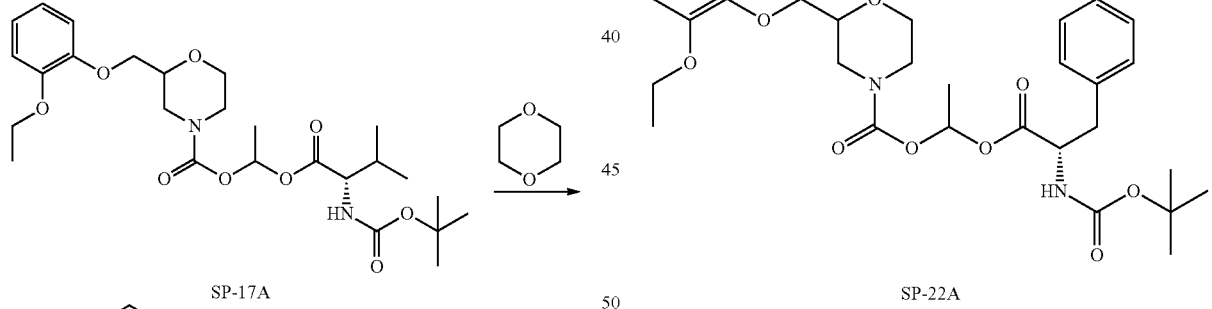

SP-22A (b) reacting SP-22A with dioxane in an organic acid

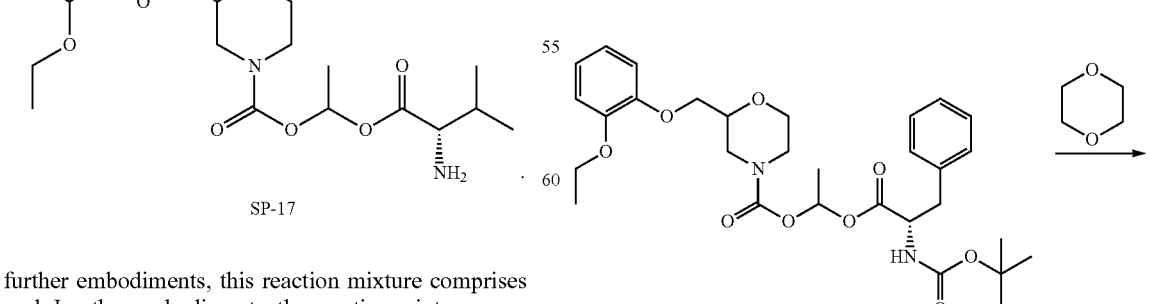

SP-22A

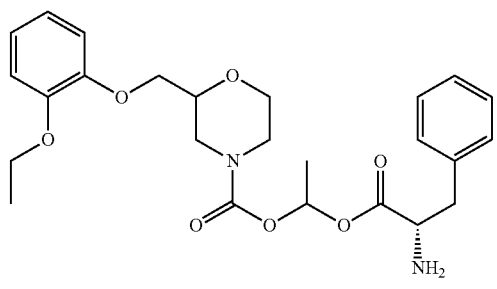

SP-22

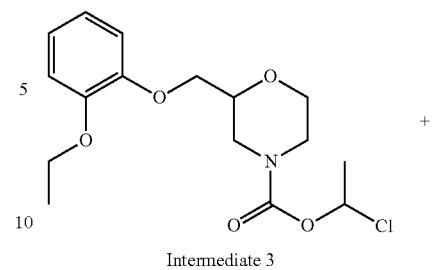

Intermediate 3

In further embodiments, this reaction mixture further comprises cesium carbonate. In other embodiments, the reaction mixture further comprises methanol. In alternative embodiments, the organic acid is hydrochloric acid.

In some embodiments, Intermediate 3 is used to prepare 1-((dimethyl-L-valyl)oxy)ethyl 2-((2-ethoxyphenoxy)methyl)morpholine-4-carboxylate (SP-23), comprising:

reacting Intermediate 3 with a reaction mixture comprising L-Val-N,N-dimethyl

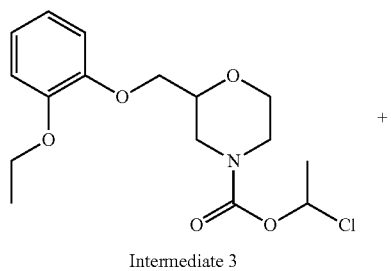

Intermediate 3

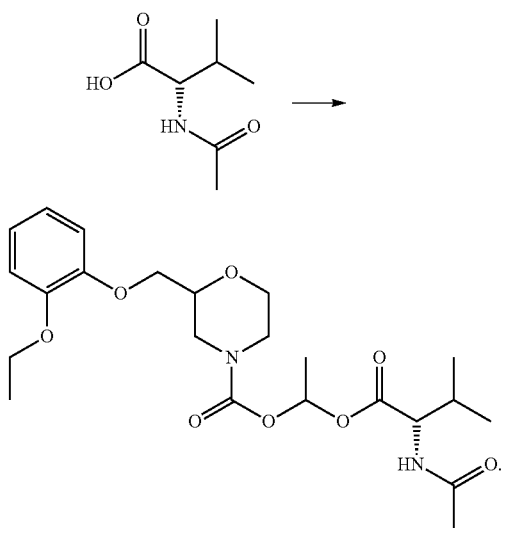

SP-24

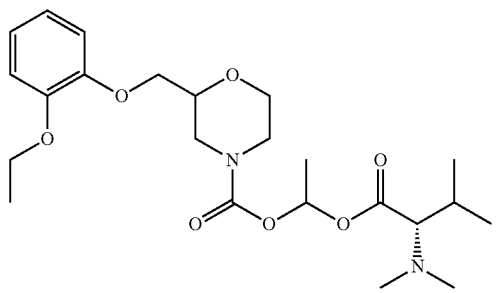

SP-23

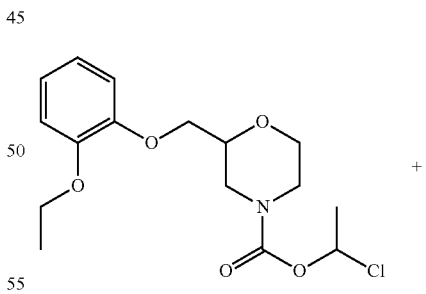

Intermediate 3

In further embodiments, this reaction mixture comprises cesium carbonate. In some embodiments, the reaction mixture comprises methanol.

In some embodiments, Intermediate 3 is used to prepare 1-((Acetyl-L-valyl)oxy)ethyl 2-((2-ethoxyphenoxy)methyl)morpholine-4-carboxylate (SP-24), comprising:

reacting Intermediate 3 with a reaction mixture comprising N-acetylvaline

In further embodiments, this reaction mixture comprises cesium carbonate. In some embodiments, the reaction mixture comprises methanol.

In some embodiments, Intermediate 3 is used to prepare 1-((methyl-D-valyl)oxy)ethyl 2-((2-ethoxyphenoxy)methyl)morpholine-4-carboxylate (SP-25), comprising:

(a) forming SP-25A by reacting Intermediate 3 with a reaction mixture comprising N-Boc-D-Valine; and

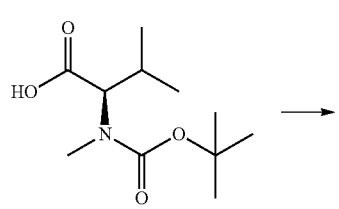

51
-continued

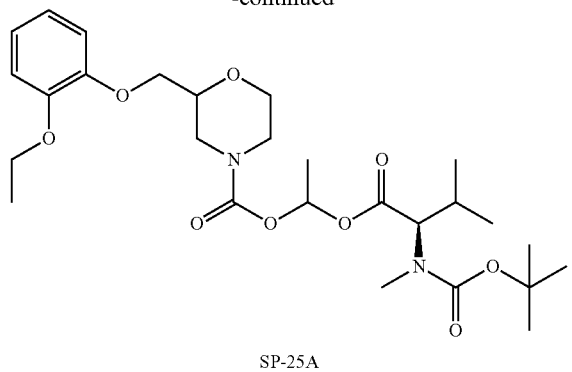

SP-25A (b) reacting SP-25A with dichloromethane and trifluoroacetic acid

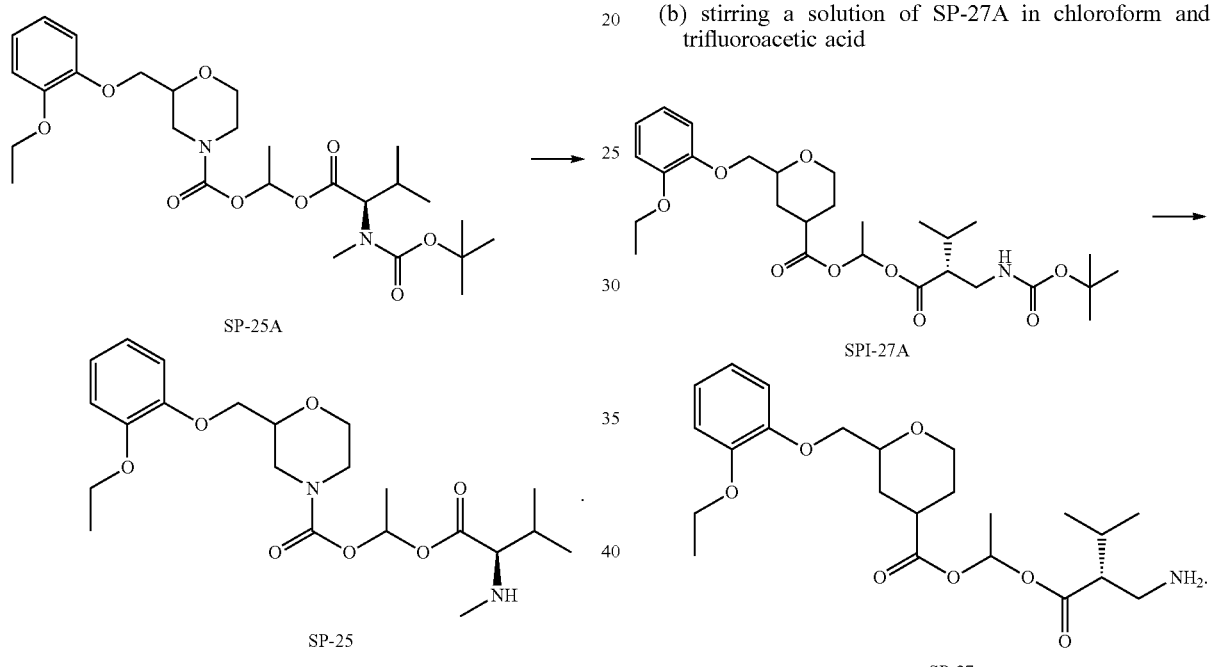

SP-25A

SP-25

In further embodiments, this reaction mixture comprises methanol. In some embodiments, the reaction mixture comprises cesium carbonate.

In some embodiments, Intermediate 3 is used to prepare 1-(((R)-2-(aminomethyl)-3-methylbutanoyl)oxy)ethyl 2-((2-ethoxyphenoxy)methyl)morpholine-4-carboxylate (SP-27), comprising:
(a) forming SP-27A by reacting Intermediate 3 and a reaction mixture comprising N-Boc-3-amino-2-isopropionic acid; and

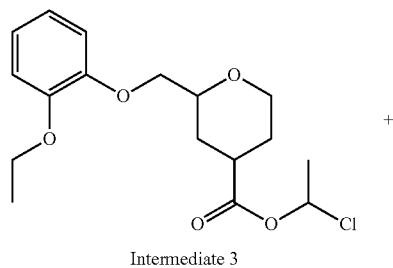

Intermediate 3

52
-continued

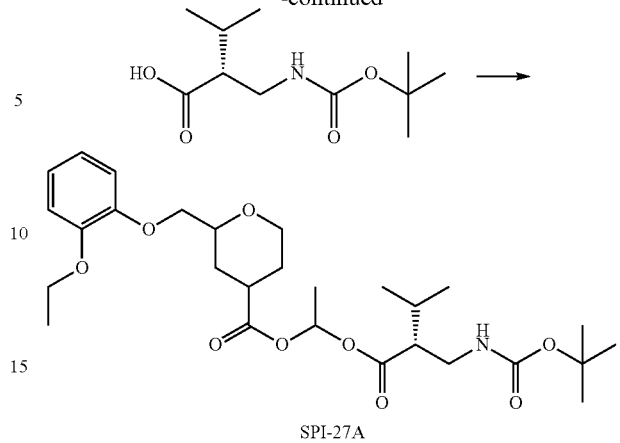

SPI-27A (b) stirring a solution of SP-27A in chloroform and trifluoroacetic acid

SPI-27A

SP-27

In further embodiments, this reaction mixture further comprises cesium carbonate. In other embodiments, the reaction mixture further comprises methanol.

In some embodiments, Intermediate 3 is used to prepare 1-(((R)-2-(aminomethyl)-3-methylbutanoyl)oxy)ethyl 2-((2-ethoxyphenoxy)methyl)morpholine-4-carboxylate (SP-28), comprising:
(a) forming SP-28A by reacting Intermediate 3 with a reaction mixture comprising Boc-Val-Val; and

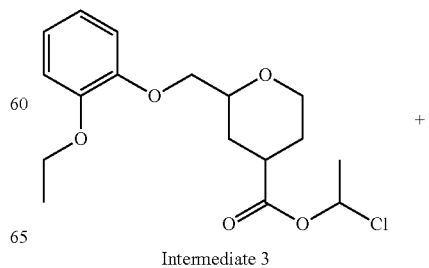

Intermediate 3

-continued

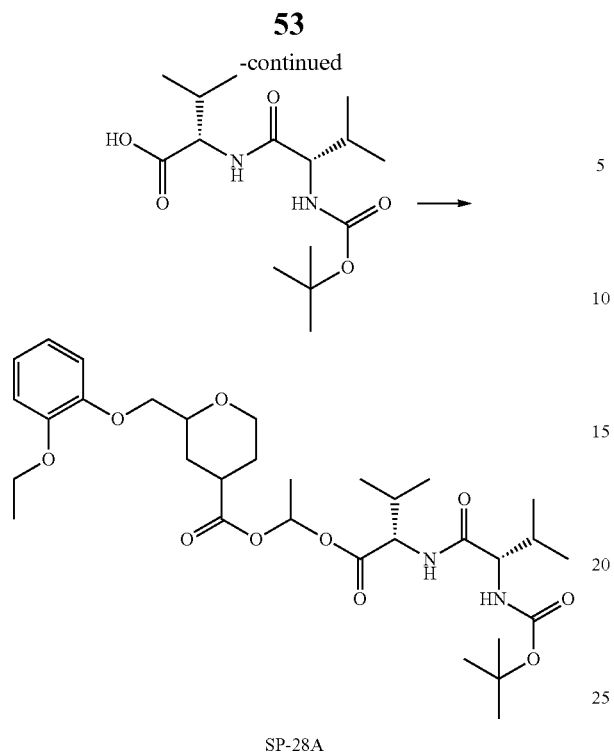

SP-28A (b) stirring a solution of SP-28A in chloroform and trifluoroacetic acid

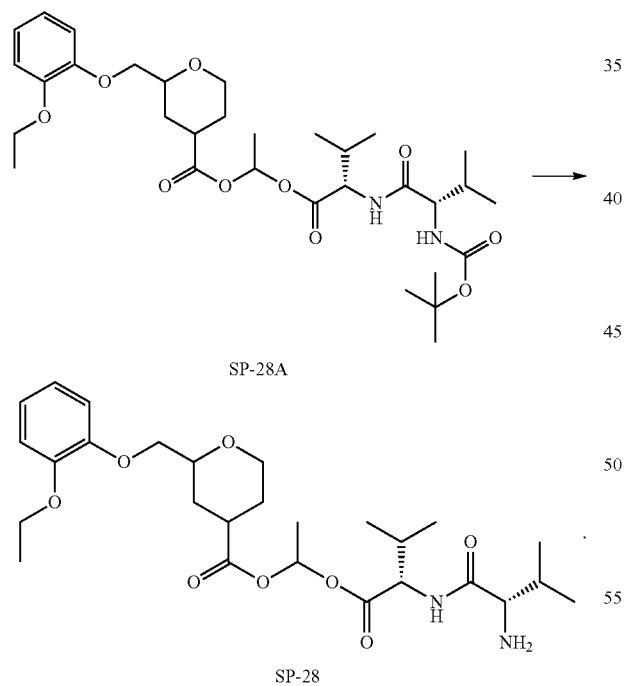

In further embodiments, this reaction mixture further comprises cesium carbonate. In some embodiments, the reaction mixture further comprises methanol.

In one embodiment, a process for preparing (2R)-2-amino-N-((2-((2-ethoxyphenoxy)methyl)morpholino)methyl)-3-methylbutanamide (SP-18) is provided, comprising:

(a) forming SP-18A by reacting 2-((2-ethoxyphenoxy)methyl)morpholine and a reaction mixture comprising polyformaldehyde; and

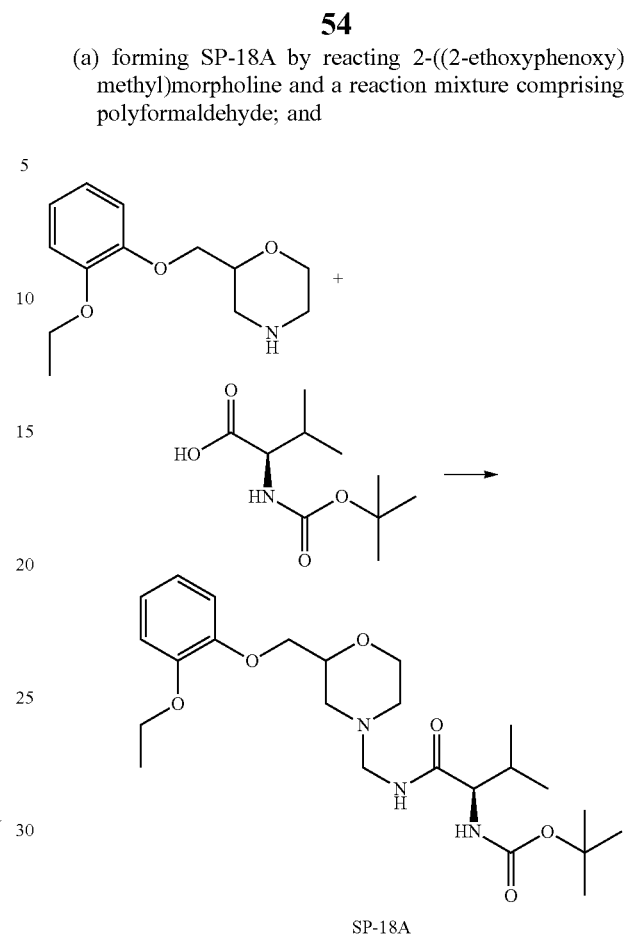

(b) reacting SP-18A with dioxane in an organic acid

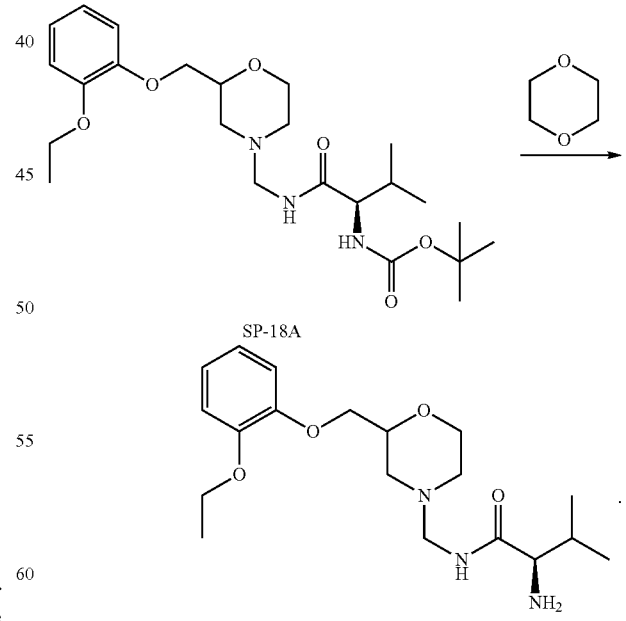

In further embodiments, this reaction mixture further comprises tetrahydrofuran. In some embodiments, the organic acid is hydrochloric acid.

In another embodiment, a process for preparing pyridine-2-yl 2((2-ethoxyphenoxy)methyl)morpholine-4-carboxylate (SP-19) is provided, comprising:

(a) forming pyridine-2-yl carbonochloridate by reacting 2-hydroxypyridine with a reaction mixture comprising N,N-diisopropylethylamine; and

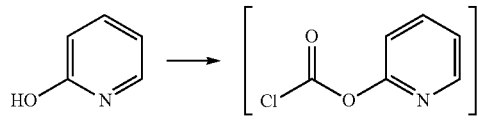

(b) reacting the pyridine-2-yl carbonochloridate with a second reaction mixture comprising 2-((2-ethoxyphenoxy)methyl)morpholine

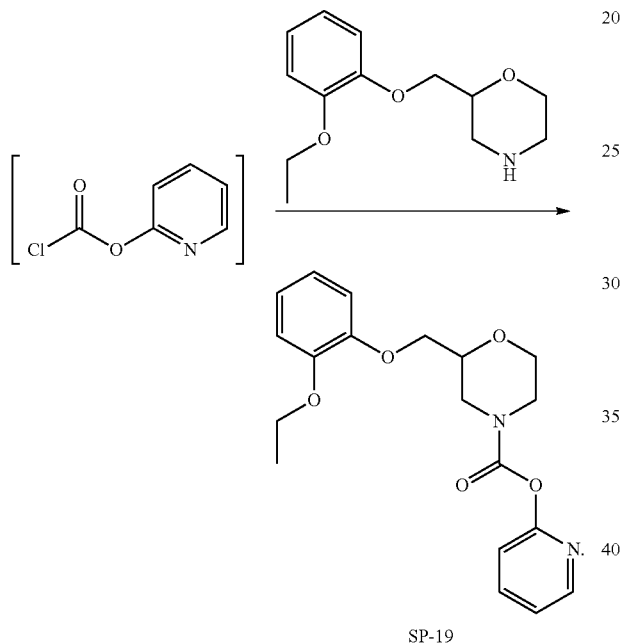

SP-19

In further embodiments, this reaction mixture comprises triphosgene. In some embodiments, the reaction mixture comprises dichloromethane. In other embodiments, the second reaction mixture comprises dichloromethane. In yet other embodiments, the second reaction mixture comprises triethylamine.

In one embodiment, a process for preparing methylene bis(2-((2-ethoxyphenoxy)methyl)morpholine-4-carboxylate (SP-21) is provided, comprising:

reacting (2-((2-ethoxyphenoxy)methyl)morpholine with a reaction mixture comprising methylene dibromide

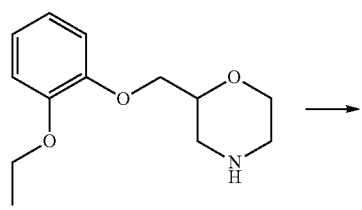

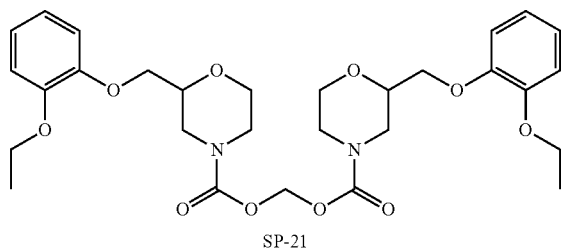

SP-21

In further embodiments, the reaction mixture comprises dimethyl formamide. In some embodiments, carbon dioxide gas is passed over the reaction mixture.

In another embodiment, a process for preparing 1-((D-valyl)oxy)-2-methylpropyl 2-((2-ethoxyphenoxy)methyl)-morphiline-4-carboxylate (SP-26) is provided, comprising:

(a) forming SP-26A by reacting (2-((2-ethoxyphenoxy)-methyl)morpholine and a first reaction mixture comprising 1-chloro-2-methylpropylchloroformate;

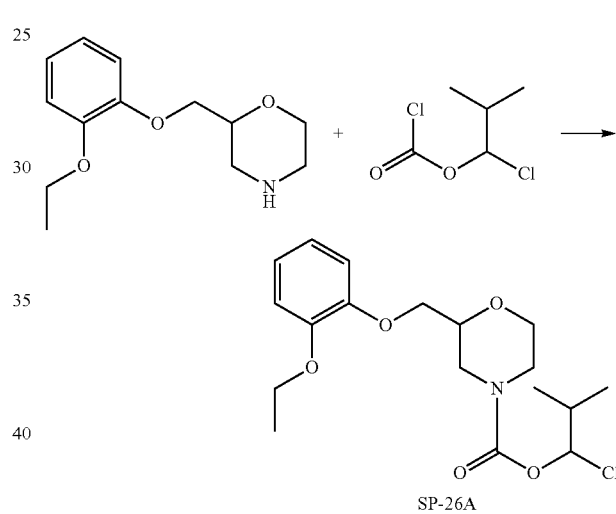

SP-26A (b) forming SP-26B by reacting SP-26A and a second reaction mixture comprising N-Boc-D-Valine; and

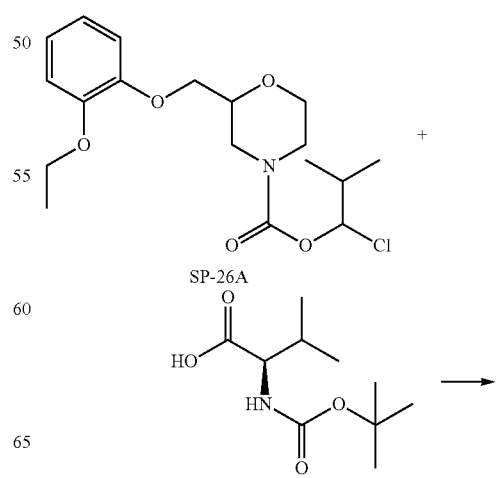

SP-26A

-continued

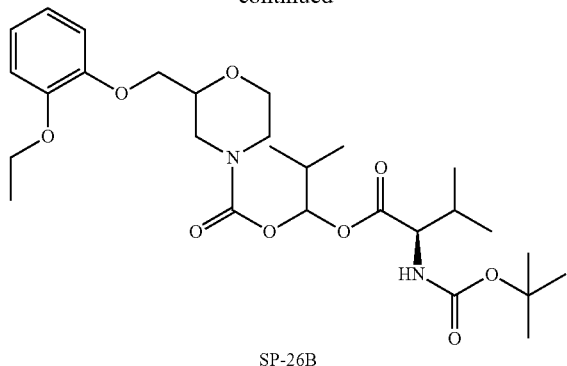
SP-26B (c) reacting SP-26B with dioxane in an organic acid

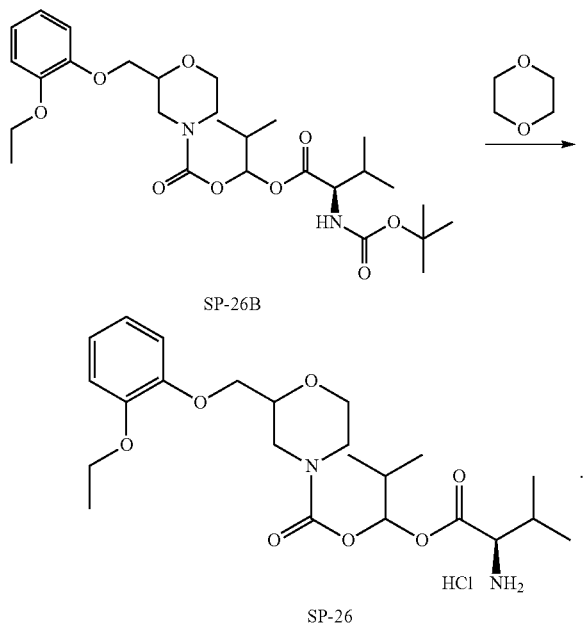
SP-26B

SP-26

In a further embodiment, the first reaction mixture comprises trimethylamine. In some embodiments, the first reaction mixture comprises dichloromethane. In other embodiments, the second reaction mixture comprises cesium carbonate. In some embodiments, the second reaction mixture comprises methanol. In other embodiments, the organic acid is hydrochloric acid.

Other embodiments are set forth in the following claims.

What is claimed is:

1. A compound of Formula I, a stereoisomer thereof, or a salt thereof:

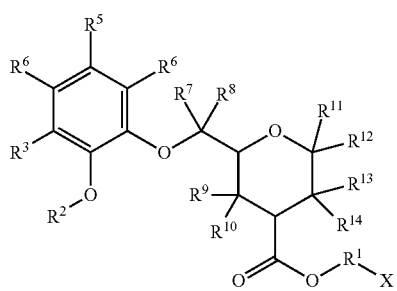
(I)

wherein:

$R^1$ is alkyl, heterocyclyl, or a pyridyl;

$R^2$ is alkyl, aryl, heteroaryl, or heterocyclyl;

$R^3$-$R^{14}$ are each independently H, F, Cl, Br, I, CN, $NO_2$, alkyl, aryl, heteroaryl, or heterocyclyl; and X is halogen, an amino acid residue with a hydrophobic side chain, or ester, wherein X may also be H only when $R^1$ is pyridyl.

2. The compound of claim 1, wherein $R^1$ is $CH_2$, $CH_2CH_2$, $CH_3CH$, $CH_2CH_2CH_2$, $CH_2CH_2CH_2CH_2$, $(CH_3)_2C$, $(CH_3)_2CHCH$, or $(CH_3)_3CCH$.

3. The compound of claim 1, wherein the amino acid residue with a hydrophobic side chain is unsubstituted.

4. The compound of claim 3, wherein the amino acid residue with a hydrophobic side chain is valine.

5. The compound of claim 4, wherein $R_1$ is $CH_2$, $CH_3CH$, or $(CH_3)_2CHCH$.

6. The compound of claim 5 that is:

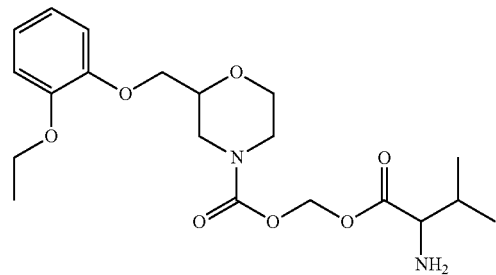

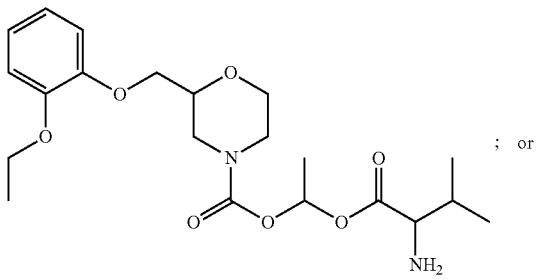

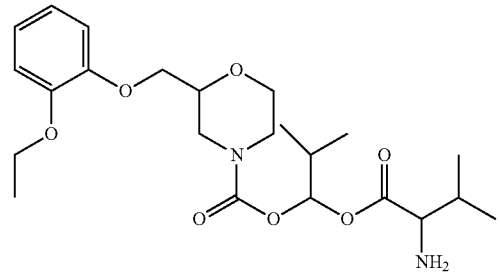

7. The compound of claim 3, wherein the amino acid residue with a hydrophobic side chain is phenylalanine.

8. The compound of claim 7, wherein $R_1$ is $CH_3CH$.

9. The compound of claim 8 having the structure

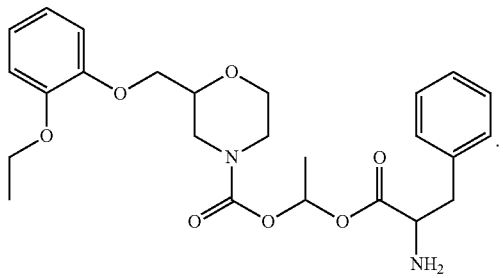 [SMILES: CCOc1ccccc1OCC1CN(C(=O)OC(C)OC(=O)C(N)Cc2ccccc2)CCO1]

10. The compound of claim 3, wherein each of $R^3$-$R^{14}$ is independently H, F, Cl, Br, I, or alkyl.

11. The compound of claim 10, wherein each of $R^3$-$R^{14}$ are each independently H or $C_1$-$C_6$ alkyl.

12. The compound of claim 11, wherein $R^3$-$R^{14}$ are all H.

13. The compound of claim 12, wherein $R^1$ is $CH_2$, $CH_2CH_2$, $CH_3CH$, $CH_2CH_2CH_2CH_2$, or $CH_3CH_2CH_2CH$, or $(CH_3)_3CCH$.

14. A compound of formula:

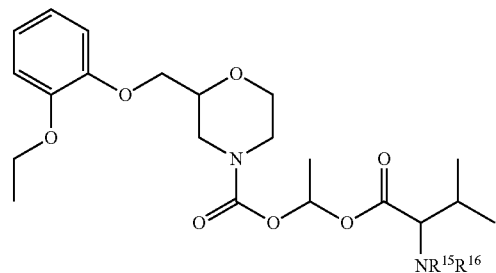

wherein:
$R^{15}$ is H, alkyl, —C(O)OR$^{17}$, or —C(O)R$^{17}$, wherein $R^{17}$ is H or alkyl; and
$R^{16}$ is H, alkyl, —C(O)OR$^{17}$, or —C(O)R$^{17}$, wherein $R^{17}$ is H or alkyl.

15. The compound of claim 14, wherein $R^{15}$ is alkyl and $R^{16}$ is H or alkyl.

16. The compound of claim 15, wherein $R^{15}$ is methyl and $R^{16}$ is H or methyl.

17. The compound of claim 16 having the structure:

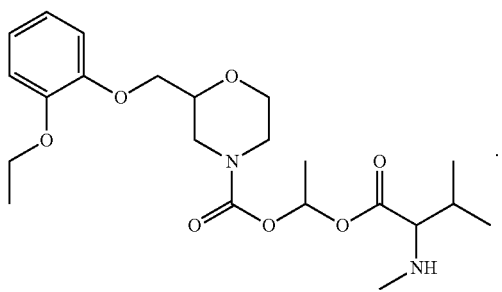 [SMILES: CCOc1ccccc1OCC1CN(C(=O)OC(C)OC(=O)C(NC)C(C)C)CCO1]

18. The compound of claim 16, wherein $R^{15}$ and $R^{16}$ are methyl.

19. The compound of claim 18 having the structure:

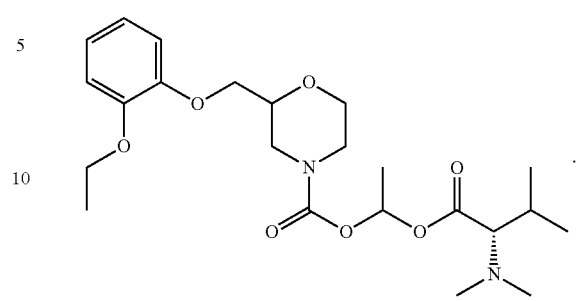

20. The compound of claim 14, wherein $R^{15}$ is —C(O)R$^{17}$ in which $R^{17}$ is methyl, and $R^{16}$ is H.

21. The compound of claim 20 having the structure:

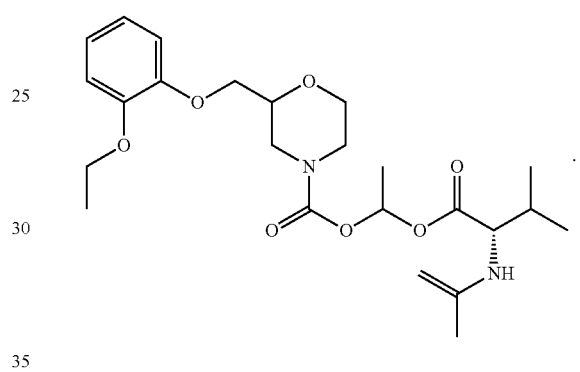

22. The compound of claim 1, wherein $R_1$ is $CH_2$ or $CH_3CH$.

23. The compound of claim 22, wherein X is an ester.

24. The compound of claim 23 which is:

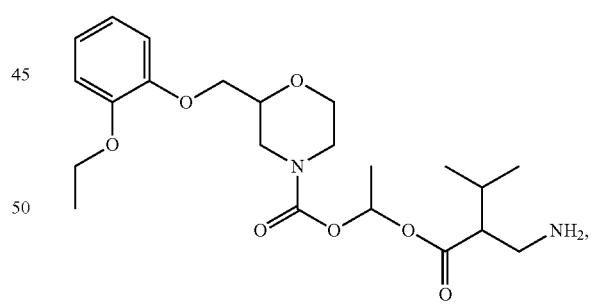

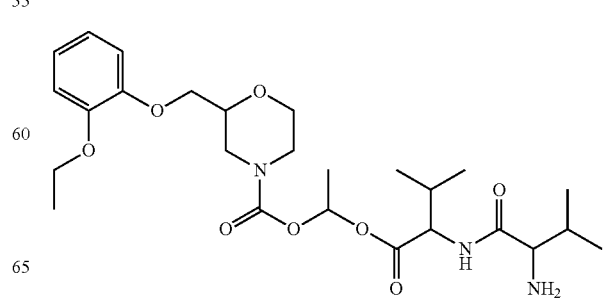

-continued
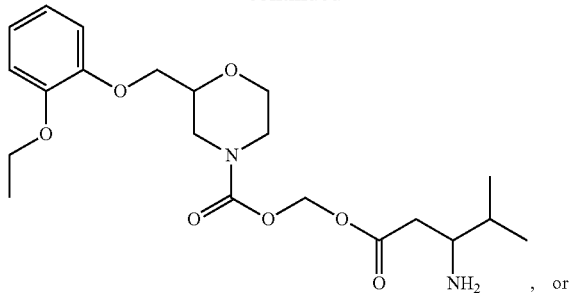, or
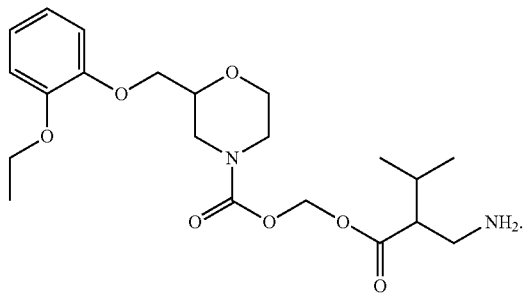.
25. The compound of claim 1 which is:
(Intermediate 2)
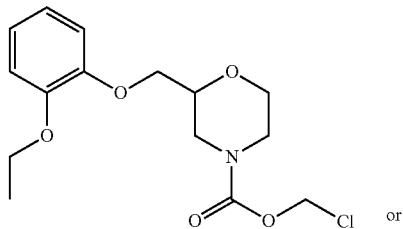 or
-continued
(Intermediate 3)
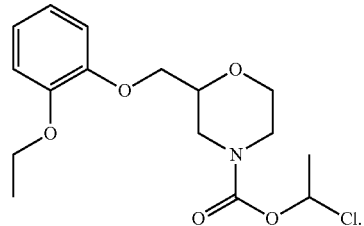.
26. The compound of claim 1, wherein $R^1$ is a pyridyl group and X is H.
27. The compound of claim 26 that is:
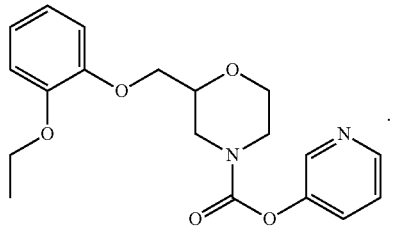 [SMILES: CCOc1ccccc1OCC1CN(C(=O)Oc2cccnc2)CCO1]
28. The compound of claim 1, wherein $R^1$ is a pyridyl group and X is F, Cl, Br, or I.
29. The compound of claim 28 that is:
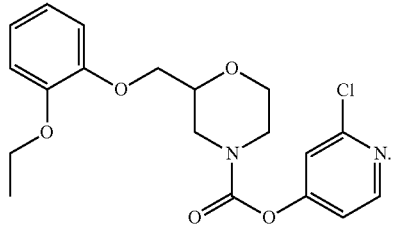 [SMILES: CCOc1ccccc1OCC1CN(C(=O)Oc2ccnc(Cl)c2)CCO1]
* * * * *

UNITED STATES PATENT AND TRADEMARK OFFICE
CERTIFICATE OF CORRECTION

| | | |
|---|---|---|
| PATENT NO. | : 11,634,415 B2 | Page 1 of 1 |
| APPLICATION NO. | : 17/824644 | |
| DATED | : April 25, 2023 | |
| INVENTOR(S) | : Janak Khimchand Padia | |

It is certified that error appears in the above-identified patent and that said Letters Patent is hereby corrected as shown below:

In the Claims

Column 60, Claim 21, Lines 20-34, replace the compound with the following:

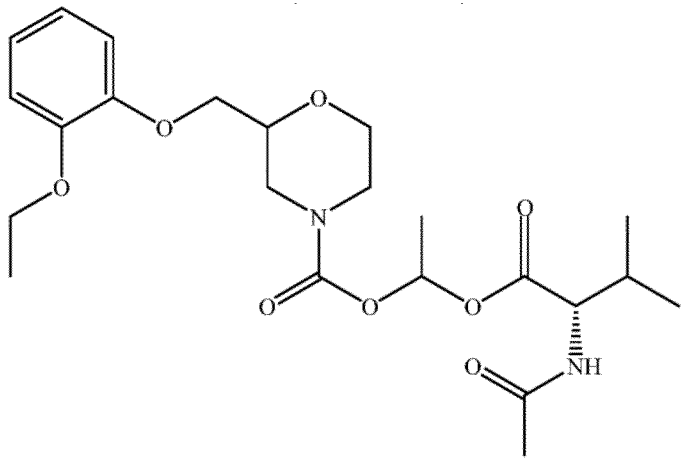

Signed and Sealed this
Fifteenth Day of July, 2025

Coke Morgan Stewart
*Acting Director of the United States Patent and Trademark Office*